(12) United States Patent
Podhajcer et al.

(10) Patent No.: US 7,067,495 B1
(45) Date of Patent: Jun. 27, 2006

(54) COMPOSITIONS AND METHODS FOR TUMOUR THERAPY

(75) Inventors: Osvaldo Luis Podhajcer, Buenos Aires (AR); Maria Fernanda Ledda, Buenos Aires (AR); Soraya Karina Adris, Buenos Aires (AR); Alicia Ines Bravo, Buenos Aires (AR); Jose Mordoh, Buenos Aires (AR); Yuti Chernajovsky, London (GB)

(73) Assignee: Fundacion Instituto Leloir, Buenos Aires (AR)

( * ) Notice: Subject to any disclaimer, the term of this patent is extended or adjusted under 35 U.S.C. 154(b) by 0 days.

(21) Appl. No.: 09/340,595

(22) Filed: Jun. 28, 1999

Related U.S. Application Data

(63) Continuation of application No. PCT/GB97/03548, filed on Dec. 24, 1997.

(60) Provisional application No. 60/038,068, filed on Feb. 12, 1997.

(30) Foreign Application Priority Data

Dec. 27, 1996 (GB) .................................. 9626989.9

(51) Int. Cl.
  *A01N 43/04* (2006.01)
  *A01N 43/16* (2006.01)
  *C12P 19/34* (2006.01)
  *C12Q 1/68* (2006.01)
  *C07H 21/04* (2006.01)

(52) U.S. Cl. ..................... 514/44; 435/6; 435/91.1; 435/455; 536/23.1; 536/24.5

(58) Field of Classification Search ............ 435/91.3, 435/91.31, 320.1, 375, 455, 6, 91.1; 514/44; 536/24.5, 23.1
See application file for complete search history.

(56) References Cited

U.S. PATENT DOCUMENTS

| | | | |
|---|---|---|---|
| 5,248,671 A | 9/1993 | Smith | 514/44 |
| 5,340,934 A | 8/1994 | Termine et al. | 536/23.5 |
| 5,442,049 A | 8/1995 | Anderson et al. | 536/24.5 |
| 5,457,189 A | 10/1995 | Crooke et al. | 536/24.5 |
| 5,801,154 A * | 9/1998 | Baracchini et al. | |
| 5,858,776 A * | 1/1999 | Ostrand-Rosenberg et al. | |
| 6,030,786 A | 2/2000 | Cowsert | 435/6 |
| 6,030,837 A | 2/2000 | McKay et al. | 435/375 |
| 6,030,954 A * | 2/2000 | Wu et al. | 514/44 |
| 6,031,086 A | 2/2000 | Switzer | 536/23.1 |
| 6,114,517 A | 9/2000 | Monia et al. | 536/24.5 |
| 6,117,847 A | 9/2000 | Bennett et al. | 514/44 |
| 6,117,848 A | 9/2000 | Monia et al. | 514/44 |
| 6,121,047 A | 9/2000 | Bennett et al. | 435/375 |
| 6,130,088 A | 10/2000 | Monia et al. | 435/375 |
| 6,133,031 A | 10/2000 | Monia et al. | 435/375 |
| 6,133,032 A | 10/2000 | Monia et al. | 435/375 |
| 6,136,603 A | 10/2000 | Dean et al. | 435/375 |
| 6,136,604 A | 10/2000 | Monia et al. | 435/375 |
| 6,140,124 A | 10/2000 | Monia et al. | 435/375 |
| 6,140,125 A | 10/2000 | Taylor et al. | 435/375 |
| 6,140,126 A | 10/2000 | Bennett et al. | 435/375 |
| 6,150,162 A | 11/2000 | Bennett et al. | 435/375 |
| 6,153,595 A | 11/2000 | Draper et al. | 514/44 |
| 6,156,571 A | 12/2000 | Bennett et al. | 435/375 |
| 6,159,694 A | 12/2000 | Karras | 435/6 |
| 6,159,697 A | 12/2000 | Monia et al. | 435/6 |
| 6,159,734 A | 12/2000 | McKay et al. | 435/375 |
| 6,165,728 A | 12/2000 | Ward et al. | 435/6 |
| 6,165,786 A | 12/2000 | Bennett et al. | 435/366 |
| 6,165,788 A | 12/2000 | Bennett et al. | 435/375 |
| 6,165,789 A | 12/2000 | Monia et al. | 435/375 |
| 6,165,790 A | 12/2000 | Borchers et al. | 435/375 |
| 6,165,791 A | 12/2000 | Popoff et al. | 435/375 |
| 6,168,950 B1 | 1/2001 | Monia et al. | 435/375 |
| 6,171,860 B1 | 1/2001 | Baker et al. | 435/375 |
| 6,177,246 B1 | 1/2001 | Monia et al. | 435/6 |
| 6,187,585 B1 | 2/2001 | Bennett et al. | 435/375 |
| 6,187,587 B1 | 2/2001 | Popoff et al. | 435/375 |
| 6,190,869 B1 | 2/2001 | Bennett et al. | 435/6 |
| 6,214,986 B1 | 4/2001 | Bennett et al. | 536/24.5 |
| 6,238,921 B1 | 5/2001 | Miraglia et al. | 435/375 |

FOREIGN PATENT DOCUMENTS

WO  WO 96/26267  8/1996

OTHER PUBLICATIONS

Ledda et al. Medicina 1996; 56:51-54.*
Green et al. J. of Am. Coll. Surg. vol. 191, No. 1, Jul. 2000.*
Flanagan et al., Nature Biotechnology, vol. 17, No. 1, pp. 48-52, Jan. 1999.*
Agrawal et al. Molecular Medicine Today, vol. 6, pp. 72-81, Feb. 2000.*
Bennett et al. "Pharmacology of Antisense Therapeutic Agents", Chapter 2, from Methods in Molecular Medicine: Antisense Therapeutics. Ed. S. Agrawal, Humana Press., Totowa, NJ, ISBN: 0_89603-305-8, 1996.*

(Continued)

Primary Examiner—Sean McGarry
Assistant Examiner—Jane Zara
(74) Attorney, Agent, or Firm—Watov & Kipnes, P.C.

(57) ABSTRACT

Compositions and methods are described that decrease or inhibit osteonectin activity in tumor cells, including cancer cells. The cells cease to be tumor-like, or become less tumor-like. Pharmaceutical composition and therapies based thereon are also described.

4 Claims, 7 Drawing Sheets

OTHER PUBLICATIONS

Ma et al., Biotechnology Annula Review, vol. 5, pp. 155-196, 2000.*

Branch, TIBS 23, pp. 45-50, Feb. 1998.*

GenEmbl database Accession No. J03040, Human SPARC/osteonectin mRNA, complete CDS, Jan. 1995.*

Crooke, S. T. Vitravene—Another Piece in the mosaic. Antisense.& Nucleic Acid Drug Devel. 8 (1998), vii-viii.*

Crystal, R.G. Transfer of genes to humans: Early lessons and obstacles to success. Science 270 (1995): 404-410.*

Gewirtz et al. Facilitating oligonucleotide delivery: Helping antisnse deliver on its promise. Proc. Natl. Acad. Sci. USA 93 (1996): 3161-3163.*

Jen et al. Suppression of gene expression by targeted disruption of messenger RNA: Available options and current strategies, Stem Cells 18 (2000): 307-319.*

Report and recommendations of the panel to assess the NIH investment in research on gene therapy, Orkin and Motulsky, co-chairs. National Institutes of Health (Dec. 1995).*

Rojanasakul, Y. Antisense oligonucleotide therapeutics: Drug delivery and targeting. Adv. Drug Delivery Rev. 18(1996): 115-131.*

Stull et al. Antigene, ribozyme,and aptamer nucleic acid drugs: Progress and prospects. Pharm. Res. 12(1995): 465-483.*

Peracchi, A. et al. Rev. Med. Virol. vol. 14, pp. 47-64 (2004).*

Crooke, S. antisense Res. and Application, Chapter 1, pp. 1-50, ed. by S. Crooke, Springer-Verlag (1998).*

Branch, A. Trends in Biochem. Sci. vol. 23, pp. 45-50 (1998).*

Chirila, T. et al. Biomaterials, vol. 23, pp. 321-342 (2002).*

Ledda, M.F., et al., "La expresión del c-DNA antientido del gen SPARC anula la capacidad tumorigénica de células de melanoma humano," *Medicina* 55:565-566, Abstract No. 267, Sociedad Argentina De Investigacion Clinica (Dec. 1995).

English language translation for Ledda, M.F., et al., "The Expression of the anitsense c-DNA of the SPARC gene annuls the tumorigenic capacity of human melanoma cells," (Dec. 1995).

Lewis, J.G., et al., "A serum-resistant cytofectin for cellular delivery of antisense oligodeoxynucleotides and plasmid DNA," *Proc. Natl. Acad. Sci. USA 93*:3176-3181, National Academy of Sciences of the USA (Apr. 1996).

Aoki, K., et al., "Liposome-mediated *in Vivo* Gene Transfer of Antisense K-ras Construct Inhibits Pancreatic Tumor Dissemination in the Murine Peritoneal Cavity," *Cancer Res. 55*:3810-3816 (Sep. 1995).

Bellahcène, A., and Castronovo, V., "Increased Expression of Osteonectin and Osteopontin, Two Bone Matrix Proteins, in Human Breast Cancer," *Amer. J. Pathol. 146*:95-100 (Jan. 1995).

Collier, I.E., et al., "H-ras Oncogene-transformed Human Bronchial Epithelial Cells (TBE-1) Secrete a Single Metalloprotease Capable of Degrading Basement Membrane Collagen," *J. Biol. Chem. 263*:6579-6587 (May 1988).

Everitt, E.A., and Sage, E.H., "Expression of SPARC is Correlated with Altered Morphologies in Transfected F9 Embryonal Carcinoma Cells," *Exp. Cell Res. 199*:134-146 (1992).

Everitt, E.A., and Sage, E.H., "Overexpression of SPARC in stably transfected F9 cells mediates attachment and spreading in $Ca^{2+}$-deficient medium," *Biochem. Cell Biol. 70*:1368-1379 (Dec. 1992).

Funk, S.E., and Sage, E.H., "The $Ca^{2+}$-binding glycoprotein SPARC modulates cell cycle progression in bovine aortic endothelial cells," *Proc. Natl. Acad. Sci. USA 88*:2648-2652 (Apr. 1991).

Funk, S.E., and Sage, E.H., "Differential effects of SPARC and Cationic SPARC Peptides on DNA Synthesis by Endothelial Cells and Fibroblasts," *J. Cell. Physiol. 154*:53-63 (Jan. 1993).

Harlow, E., and Lane, D., "Chapter 5: Immunizations," in *Antibodies: A Laboratory Manual*, Cold Spring Harbor Laboratory Press, Cold Spring Harbor, NY, pp. 53-137 (1988).

Kamihagi, K., et al., "Osteonectin/SPARC Regulates Cellular Secretion Rates of Fibronectin and Laminin Extracellular Matrix Proteins," *Biochem. Biophys. Res. Comm. 200*:423-428 (Apr. 1994).

Laird, A.D., et al., "Inhibition of Tumor Growth in Liver Epithelial Cells Transfected with a Transforming Growth Factor α Antisense Gene," *Cancer Res. 54*:4224-4232 (Aug. 1994).

Lane, T.F., and Sage, E.H., "Functional Mapping of SPARC: Peptides from Two Distinct $Ca^{++}$-binding Sites Modulate Cell Shape," *J. Cell Biol. 111*:3065-3076 (Dec. 1990).

Lane, T.F., et al., "Regulation of Gene Expression by SPARC during Angiogenesis *in Vitro*," *J. Biol. Chem. 267*:16736-16745 (Aug. 1992).

Lane, T.F., and Sage, E.H., "The Biology of SPARC, a protein that modulates cell-matrix interactions," *FASEB J. 8*:163-173 (Feb. 1994).

Lane, T.F., et al., "SPARC Is a Source of Copper-binding Peptides that Stimulate Angiogenesis," *J. Cell Biol. 125*:929-943 (May 1994).

Ledda, M.F., et al., "Expression of SPARC in melanoma and dysplastic nevi," *Proceedings of the American Association for Cancer Research Annual Meeting 36*:63 (1995).

Ledda, M.F., et al., "Rol del Gen SPARC en la Capacidad Tumorigenica de Celulas de Melanoma Humano," *Medicina (Buenos Aires)* 56:51-54 (1996)(English translation attached—Ledda, M.F., et al., "The role of SPARC gene in the tumorigenic capacity of human melanoma cells").

Ledda, F., et al., "The Expression of the Secreted Protein Acidic and Rich in Cysteine (SPARC) Is Associated with the Neoplastic Progression of Human Melanoma," *J. Invest. Dermatol. 108*:210-214 (Feb. 1997).

Ledda, M.F., et al., "Suppression of SPARC expression by antisense RNA abrogates the tumorigenicity of human melanoma cells," *Nature Med. 3*:171-176 (Feb. 1997).

Mason, I.J., et al., "Evidence from molecular cloning that SPARC, a major product of the mouse embryo parietal endoderm, is related to an endothelial cell 'culture shock' glycoprotein of M, 43 000," *EMBO J. 5*:1465-1472 (Jul. 1986).

Maurer, P., et al., "High-affinity and low-affinity calcium binding and stability of the multidomain extracellular 40-kDa basement membrane glycoprotein (BM-40/SPARC/osteonectin)," *Eur. J. Biochem. 205*:233-240 (Apr. 1992).

Mercola, D., and Cohen, J.S., "Antisense approaches to cancer gene therapy," *Cancer Gene Ther. 2*:47-59 (Mar. 1995).

Mok, S.C., et al., "SPARC, an extracellular matrix protein with tumor-suppressing activity in human ovarian epithelial cells," *Oncogene 12*:1895-1901 (May 1996).

Podhajcer, O.L., et al., "Comparative expression of the SPARC and stromelysin-3 genes in mammary tumours," *The Breast* 5:13-20 (Feb. 1996).

Podhajcer, O.L., et al., "Expression of Cathepsin D in Primary and Metastatic Human Melanoma and Dyaplastic Nevi," *J. Invest. Dermatol.* 104:340-344 (Mar. 1995).

Porte, H., et al., "Neoplastic Progression of Human Colorectal Cancer is Associated with Overexpression of the Stromelysin-3 and *BM-40/SPARC* Genes," *Int. J. Cancer.* 64:70-75 (Feb. 1995).

Porter, P.L., et al., "Distribution of SPARC in Normal and Neoplastic Human Tissue," *J. Histochem. Cytochem.* 43:791-800 (Aug. 1995).

Pottgiesser, J., et al., "Changes in Calcium and Collagen IV Binding Caused by Mutations in the EF Hand and Other Domains of Extracellular Matrix Protein BM-40 (SPARC, Osteonectin)," *J. Mol. Biol.* 238:563-574 (May 1994).

Sage, H., et al., "SPARC, A Secreted Protein Associated with Cellular Proliferation, Inhibits Cell Spreading In Vitro and Exhibits $Ca^{+2}$-dependent Binding to the Extracellular Matrix," *J. Cell Biol.* 109:341-356 (Jul. 1989).

Sage, E.H., and Bornstein, P., "Extracellular Proteins That Modulate Cell-Matrix Interactions," *J. Biol. Chem.* 266:14831-14834 (Aug. 1991).

Sage, E.H., "Terms of attachment: SPARC and tumorigenesis," *Nature Med.* 3:144-146 (Feb. 1997).

Swaroop, A., et al., "Molecular Analysis of the cDNA for Human SPARC/Osteonectin/BM-40: Sequence, Expression and Localization of the Gene to Chromosome 5q31-q33," *Genomics* 2:37-47 (Jan. 1988).

Tremble, P.M., et al., "SPARC, a Secreted Protein Associated with Morphogenesis and Tissue Remodeling, Induces Expression of Metalloproteinases in Fibroblasts Through a Novel Extracellular Matrix-dependent Pathway," *J. Cell Biol.* 121:1433-1444 (Jun. 1993).

Trojan, J., et al., "Treatment and Prevention of Rat Glioblastoma by Immunogenic C6 Cells Expression Antisense Insulin-Like Growth Factor I RNA," *Science* 259:94-97 (Jan. 1993).

International Search Report for PCT/GB97/03548, mailed Jul. 16, 1998.

* cited by examiner

SEQUENCE LISTING

<160> NUMBER OF SEQ ID NOS: 2

<210> SEQ ID NO 1
<211> LENGTH: 2133
<212> TYPE: DNA
<213> ORGANISM: Homo sapiens

<400> SEQUENCE: 1

| | | | | | |
|---|---|---|---|---|---|
| cgggagagcg | cgctctgcct | gccgcctgcc | tgcctgccac | tgagggttcc | cagcaccatg | 60 |
| agggcctgga | tcttctttct | cctttgcctg | gccgggaggg | ccttggcagc | ccctcagcaa | 120 |
| gaagccctgc | ctgatgagac | agaggtggtg | aagaaactg | tggcagaggt | gactgaggta | 180 |
| tctgtgggag | ctaatcctgt | ccaggtgaa | gtaggagaat | tgatgatgg | tgcagaggaa | 240 |
| accgaagagg | aggtggtggc | ggaaaatccc | tgccagaacc | accactgcaa | acacggcaag | 300 |
| gtgtgcgagc | tggatgagaa | caacaccccc | atgtgcgtgt | gccaggaccc | caccagctgc | 360 |
| ccagccccca | ttggcgagtt | tgagaaggtg | tgcagcaatg | acaacaagac | cttcgactct | 420 |
| tcctgccact | tctttgccac | aaagtgcacc | ctggagggca | ccaagaaggg | ccacaagctc | 480 |
| cacctggact | acatcgggcc | ttgcaaatac | atcccccctt | gcctggactc | tgagctgacc | 540 |
| gaattccccc | tgcgcatgcg | ggactggctc | aagaacgtcc | tggtcaccct | gtatgagagg | 600 |
| gatgaggaca | caaccttct | gactgagaag | cagaagctgc | gggtgaagaa | gatccatgag | 660 |
| aatgagaagc | gcctggaggc | aggagaccac | cccgtggagc | tgctggcccg | ggacttcgag | 720 |
| aagaactata | acatgtacat | cttccctgta | cactggcagt | tcggccagct | ggaccagcac | 780 |
| cccattgacg | gtacctctc | ccacaccgag | ctggctccac | tgcgtgctcc | cctcatcccc | 840 |
| atggagcatt | gcaccacccg | cttttcgag | acctgtgacc | tggacaatga | caagtacatc | 900 |
| gccctggatg | agtgggccgg | ctgcttcggc | atcaagcaga | aggatatcga | caaggatctt | 960 |
| gtgatctaaa | tccactcctt | ccacagtacc | ggattctctc | tttaaccctc | cccttcgtgt | 1020 |
| ttcccccaat | gtttaaaatg | tttggatggt | tgttgttct | gcctggagac | aaggtgctaa | 1080 |
| catagattta | agtgaataca | ttaacggtgc | taaaaatgaa | aattctaacc | caagacatga | 1140 |
| cattcttagc | tgtaacttaa | ctattaaggc | cttttccaca | cgcattaata | gtcccatttt | 1200 |
| tctcttgcca | tttgtagctt | tgcccattgt | cttattggca | catgggtgga | cacggatctg | 1260 |
| ctgggctctg | ccttaaacac | acattgcagc | ttcaactttt | ctctttagtg | ttctgtttga | 1320 |
| aactaatact | taccgagtca | gactttgtgt | tcatttcatt | tcagggtctt | ggctgcctgt | 1380 |
| gggcttcccc | aggtggcctg | gaggtgggca | aagggaagta | acagacacac | gatgttgtca | 1440 |
| aggatggttt | tgggactaga | ggctcagtgg | tgggagagat | ccctgcagaa | tccaccaacc | 1500 |
| agaacgtggt | ttgcctgagg | ctgtaactga | gagaaagatt | ctgggctgt | cttatgaaaa | 1560 |
| tatagacatt | ctcacataag | cccagttcat | caccatttcc | tcctttacct | ttcagtgcag | 1620 |
| tttcttttca | cattaggctg | ttggttcaaa | cttttgggag | cacggactgt | cagttctctg | 1680 |
| ggaagtggtc | agcgcatcct | gcagggcttc | tcctcctctg | tcttttggag | aaccagggct | 1740 |
| cttctcaggg | gctctaggga | ctgccaggct | gtttcagcca | ggaaggccaa | aatcaagagt | 1800 |
| gagatgtaga | aagttgtaaa | atagaaaaag | tggagttggt | gaatcggttg | ttctttcctc | 1860 |
| acatttggat | gattgtcata | aggttttag | catgttcctc | cttttcttca | ccctcccctt | 1920 |
| tgttcttcta | ttaatcaaga | gaaacttcaa | agttaatggg | atggtcggat | ctcacaggct | 1980 |
| gagaactcgt | tcacctccaa | gcatttcatg | aaaaagctgc | ttcttattaa | tcatacaaac | 2040 |

```
tctcaccatg atgtgaagag tttcacaaat ctttcaaaat aaaaagtaat gacttagaaa    2100
ctgaaaaaaa aaaaaaaaaa aaaaaaaaaa aaa                                 2133
```

<210> SEQ ID NO 2
<211> LENGTH: 5
<212> TYPE: PRT
<213> ORGANISM: Unknown
<220> FEATURE:
<223> OTHER INFORMATION: Cu2+ binding sequence

<400> SEQUENCE: 2

```
Lys Lys Gly His Lys
1               5
```

COMPOSITIONS AND METHODS FOR TUMOUR THERAPY

CROSS-REFERENCE TO RELATED APPLICATIONS

This is a continuation of International Application PCT/GB97/03548, which has an International filing date of Dec. 24, 1997, which claims benefit of Provisional application Ser. No. 60/038,068, filed Feb. 12, 1997.

FIELD OF THE INVENTION

This invention relates to compositions and methods for tumour therapy, in particular to pharmaceutical compositions and methods for cancer therapy. More particularly, the invention relates to the regulation of cellular activity dependent on the action of osteonectin, and to vectors therefor. The invention also relates to pharmaceutical compositions based on such vectors, to production of cells transduced or transfected with such vectors and their expression products, to pharmaceutical preparations based on such cells, to their use for administration to humans and non-human animals, to their use in order to express foreign genetic material in vivo and in vitro, and to the use of materials as described herein for the manufacture of preparations for treatment and other applications as mentioned herein.

BACKGROUND OF THE INVENTION

Osteonectin is a known protein, otherwise designated as SPARC (secreted protein, acidic and cysteine-rich), or as BM40 and 43 Kd. It is a secreted glycoprotein widely distributed in human and non-human animal tissues. It is associated with cell populations exhibiting high rates of turnover and remodelling [5,6]. The protein is secreted by different normal cells as a unique glycoprotein band of 40–44 kDa [5]. It has been shown that in addition to a reactive protein doublet of 40–45 kDa, osteonectin can appear in fresh melanoma samples and cell lines as a cleaved protein doublet of 34–35 kDa. Genes that encode osteonectin in several species, including the human, are also known. The gene encoding osteonectin is known to be highly conserved across a wide range of living organisms.

A diverse range of functions and effects has been associated with osteonectin. It has been found to interact with extracellular matrix components, growth factors, cytokines, and to regulate matrix metalloproteinase expression.

The literature of oncology includes numerous mentions of osteonectin and its synonyms. In particular, reports from different laboratories indicate that osteonectin over-expression was associated with neoplastic progression of different malignant tumours [8–12], including human melanoma. Porter et al [8] previously reported increased SPARC expression in ovary cancer cells, but on the other hand Mock et al have reported that SPARC expression is down-regulated in ovary cancer cells compared to normal cells [27], and that moreover the stable over-expression in ovary cancer cell lines of SPARC, secreted as a unique species of 43 kDa. reduced their growth capacity [27]. Molecular analysis of SPARC's role in cell growth thus has to take into account studies (including data of the present inventors) showing no effect on melanoma cell growth following SPARC down-regulation.

Osteonectin expression has been reported to be correlated with lung colonization by tumours. Increased expression has been reported in human breast cancer. Neoplastic progression of colorectal cancer has been reported as associated with over-expression of certain proteins including osteonectin.

Osteonectin has been reported as having effects on tumour cell adhesion and invasion. One view concerning cell-matrix interaction in tumour progression indicates that inhibition of tumour cell adhesion can result in less aggressive invasive behaviour. Adhesive proteins like fibronectin, vitronectin and laminin can regulate metastatic activity, invasive capacity and collagenase IV production of human and murine melanoma cells [13–16]. Osteonectin by contrast is considered to be a counteradhesive protein involved in matrix deposition and assembly due to its interaction with collagens types I–V [5,6,17], thrombospondin [5,18] and plasminogen [18] and the regulation of the expression levels of laminin [19], fibronectin [18,19], matrix metalloproteinases [7] and plasminogen activator inhibitor-1 [18].

Domains I and IV of SPARC, which can be specifically cleaved and released by different serine proteases [20], have been found responsible for SPARC binding to collagen IV and for disruption of focal cell adhesions [21,22].

Native SPARC and a specific peptide corresponding to domain II which exhibit sequence similarity with EGF-like domains have been shown to inhibit endothelial cell proliferation [23]. However, a second peptide corresponding to another region of domain II containing the $Cu^{2+}$ binding sequence KKGHK [SEQ ID NO:2] which promotes cell growth and angiogenesis [24] stimulated endothelial cells and fibroblast proliferation [23].

Sage and colleagues reported that SPARC was able to inhibit DNA synthesis in endothelial cells, through a mechanism which did not involve changes in cell morphology [28]. Their evidence that peptides corresponding to domain II of SPARC can stimulate cell proliferation [23], suggests that the extracellular cleavage may have important consequences on the ability of SPARC to modulate cell growth. On the other hand, SPARC obtained from bovine bone, which efficiently modulated laminin and fibronectin secretion, was reported to have negligible effects on cell growth of different human malignant cell lines [19]. Stable over- or under-expression of SPARC in F9 cells, which correlated with altered morphologies in transfected cells, was reported not to affect cell growth [29]. In general, SPARC interaction with and regulation of the expression levels of matrix components seems to occur in the absence of any significant effect on cell growth [5,6]. Taken together, data from the literature and data of the present findings suggest that SPARC inhibition of cell growth can be related to specific cell types, probably independent of its modulation of cell matrix interaction.

Tumour cell rejection has been associated with a localized and massive inflammatory infiltrate of segmented neutrophils suggesting an increased availability of neutrophil trigger factors like IL-8 or the autocrine melanoma growth stimulating activity (MGSA/GRO) [30]. Matrix components like laminin were shown to modulate the availability of cytokines and chemokines [31] indicating that changes in matrix composition or in the interactions between tumour cells and matrix components may alter the immunological signals transduced to the immune system.

The concept of antisense strategies involving oligodeoxynucleotides and plasmid-derived RNA has previously been proposed as an attractive mode of anticancer gene therapy [32].

In certain cases the constitutive expression of antisense RNA coding for particular oncogenes and growth factors has been reported to be effective in the induction of reduced tumorigenicity or of in vitro malignant characteristics [33–36]. But, with few exceptions, complete suppression of tumour formation has not been achieved [32]. There thus remains a need for further materials and methods that can be used in the characterization and therapy of malignant disease and the modulation of tumour cell activity.

The present inventors have found that cellular downregulation of osteonectin in tumour cells can be associated with loss of tumorigenic effect, and that the effect can be transmitted from downregulated tumour cells to neighbouring untreated tumour cells. Downregulation of osteonectin can in particular cause a decrease in in-vitro adhesive and invasive capacity of tumour cells, and the present inventors consider that this is usefully connected with the loss of tumorigenic effect.

For example, it has been found that SPARC (osteonectin) inhibition in melanoma cells can suppress their tumorigenic capacity, providing the ability to use SPARC gene targeting for antisense therapy of human melanoma.

Evidence has been found, in particular, that SPARC (osteonectin) plays a key role in the tumorigenic capacity of human melanoma. It has been found for example that down-regulation of SPARC completely prevented tumour formation in nude mice. This effect was accompanied by a massive immune response in vivo and a strong decrease in the in vitro adhesive and invasive capacity of tumour cells. The present inventors have observed that with SPARC antisense-transfected cells no initial tumour formation was visible and tumour cell necrosis was observed very rapidly. This indicates that SPARC antisense-transfected cells were impaired in their ability to establish early tumour growth.

SUMMARY OF THE INVENTION

Accordingly, the present invention provides materials including vectors for down-regulating osteonectin and processes for their use in transforming human and animal cells, particularly malignant cells, to downregulate osteonectin. Included in the invention is the provision of materials and methods to produce transfer of genetic material, with applicability to a useful range of target cell types to downregulate osteonectin. Materials provided according to the invention include materials that can be used as vaccines for tumour immunotherapy.

DETAILED DESCRIPTION OF THE INVENTION

The invention thus provides a pharmaceutical composition, for use in tumour therapy, comprising an inhibitor of osteonectin and a pharmaceutically acceptable carrier. The inhibitor may have an activity selected from decreasing expression of osteonectin in tumour cells, decreasing secretion of osteonectin from tumour cells, reducing the activity of osteonectin expressed in tumour cells, binding to a target of osteonectin and binding to osteonectin itself.

In an embodiment of the invention wherein the inhibitor prevents or decreases expression of osteonectin. Optionally, this may be achieved by an inhibitor which prevents or decreases transcription of osteonectin DNA, or prevents or decreases translation of osteonectin mRNA into osteonectin. Specifically, said inhibitor comprises a polynucleotide able to bind to osteonectin mRNA so as to prevent or decrease translation of said mRNA into osteonectin.

A specific embodiment of the invention, described in detail below, is an antisense RNA complimentary to osteonectin mRNA. Antisense DNA is also suitable.

It is further convenient for the inhibitor of the invention to be conjugated to or administered in combination with a carrier molecule. Preferably, said carrier molecule has a function selected from increasing solubility of the inhibitor, increasing uptake into a cell of the inhibitor, slowing or preventing breakdown of the inhibitor, and facilitating manufacture of the inhibitor.

In a further embodiment of the invention, the inhibitor blocks initiation of transcription of osteonectin at the gene level.

An antisense polynucleotide of the invention is provided, able to bind to osteonectin mRNA so as to prevent or reduce translation of said mRNA by a cell. The polynucleotide is preferably selected from DNA and RNA. The invention provides inter alia: antisense polynucleotide encoding RNA or DNA that is complementary to mRNA encoding osteonectin. According to the invention the antisense polynucleotide can be used for cellular downregulation of osteonectin, and can also be used for cellular downregulation of osteonectin and transmission of loss of tumorigenic effect from downregulated cells to neighbouring untreated cells.

In a further aspect of the invention there is provided a method of tumour therapy comprising administering to a patient an effective amount of an inhibitor of osteonectin. In use the inhibitor is taken up by tumour cells, such as cancer cells, with subsequent tumour amelioration.

The invention further provides vectors for transfer of heterologous genetic material into a cell, comprising the antisense polynucleotide: e.g. viral and non-viral vectors. The vectors can be used according to the invention for transforming human and animal cells, e.g. malignant cells, to downregulate osteonectin. A still further aspect of the invention provides a vector, for use in tumour cell therapy, capable of transferring genetic material into a cell, wherein expression of said genetic material results in a decrease or inhibition of osteonectin activity in the cell.

Also provided by the invention are vaccine compositions for tumour immunotherapy, comprising vectors as mentioned herein. The vaccines can also contain further components such as carriers, excipients, and adjuvants.

Cells treated ex-vivo with the antisense polynucleotide can be used according to the invention to downregulate the effects of osteonectin protein.

The invention also provides cells comprising the downregulator arranged so as to express constitutively the downregulatory antisense nucleic acid.

According to an aspect of the invention there is provided a material to regulate cellular activity that is dependent on the action of osteonectin, for example to downregulate the effects of osteonectin protein in cells. The material can for example comprise a vector containing nucleic acid that encodes a downregulator for osteonectin. Such a downregulator can for example comprise nucleic acid encoding antisense RNA against osteonectin mRNA. In useful examples the downregulator can be arranged, e.g. with a CMV IE promoter or other suitable promoter, so that the downregulatory antisense nucleic acid can be constitutively expressed as RNA in the treated cell.

According to a further aspect of the invention there are provided cells in which the effects of osteonectin protein have been downregulated by treatment according to the invention, e.g. so that they carry and transcribe DNA encoding antisense RNA complementary to osteonectin mRNA.

Vectors according to the invention can be for example plasmids or viral vectors, e.g. recombinant viral vectors based on retroviruses, adenoviruses, herpesviruses, and/or others, encoding a nucleic acid sequence that is downregulatory for osteonectin. Such a downregulatory nucleic acid sequence can for example comprise antisense nucleic acid against osteonectin-encoding nucleic acid, e.g. DNA encoding antisense RNA against osteonectin mRNA.

Also provided by the invention is naked DNA, e.g. DNA oligonucleotides encoding antisense for osteonectin, and corresponding DNA enveloped or encapsulated in non-viral delivery compositions, e.g. in liposomes. Alternative embodiments encode antisense for osteonectin in plasmid-derived RNA.

Such vectors and other materials provided according to the invention can be used either in-vivo or ex-vivo.

Examples of vectors as provided herein can be used for direct injection of solid tumours. Examples of vectors as provided herein can be used for ex-vivo transfection of cells (e.g. tumour cells). Cells transfected ex-vivo can be used for infusion into a subject to be treated, optionally after culture and/or cell killing, e.g. by irradiation. The transfected cells can also be transfected with a gene that renders them selectively sensitive to killing by a pharmaceutical agent that is given to the animal that contains the transfected cells. An example is a herpesviral TK gene, rendering cells that harbour it sensitive to killing by (for example) ganciclovir. Thus, cells treated with an agent to downregulate osteonectin can be used, according to the invention, as vaccine for tumour immunotherapy, e.g. especially for melanomas and metastatic tumours derived from melanomas, tumours of neural tissue, and/or mammary tumours and tumours of endothelial tissue; and e.g. for malignant tumours; ovarian cancers being less-preferred subjects of treatment. Thus the source cells before treatment to down-regulate osteonectin can be of a wide range of types, including in particular the tissue types mentioned in reference [8] (Porter et al), and malignant tissue also of mesenchymal origin. According to the invention, downregulation of osteonectin can also be applied to the inhibition of angiogenesis for purposes of tumour treatment and other purposes.

Furthermore, according to the invention cytotoxic T-cells can be activated and/or expanded, e.g. in vitro, e.g. for purposes of cancer immunotherapy, by the use of transduced presenting or target cells, where the virus used for transduction of the presenting or target cells is a vector as described herein carrying genetic material encoding a downregulator of osteonectin, and in addition, if desired, encoding an immunomodulatory protein. After such treated cells have been used to activate and expand T-lymphocytes, the lymphocytes can subsequently be reinfused into a subject to be treated.

One method of using the vectors, provided by this invention, is to prepare a cellular immunogen such as a vaccine from tumour cells derived from one or more individuals by treating such tumour cells with a vector for downregulating osteonectin, and to administer this as an immunogen or vaccine for treatment of other subjects, e.g. patients. If a CTL response against the tumour cells is desired, however, for the reasons outlined above, the target antigens should be presented in the context of the correct MHC molecules. An immunogen or vaccine prepared from a tumour of one individual may not always therefore be appropriate for another individual with a different MHC type. Since MHC molecules vary from individual to individual, it is generally necessary, in order to activate CTL responses against the target antigens, to present the relevant target antigen to the immune system in the correct MHC context. Thus for use as an immunogen such as a therapeutic vaccine, in general it is considered that the selected target antigen is best introduced into the treated subject's or patient's own cells in order to generate an appropriate CTL response.

It can therefore be especially useful to base the tumour immunogen or vaccine on a patient's own tumour cells, a procedure known as autologous vaccination. A further major advantage of this technique that it can take advantage of antigenic targets that may be unique to a particular tumour; it is considered that the deregulated cell cycle control that is the basis of tumour growth can, over a period of time, lead to the accumulation of genetic changes manifested as new antigenic determinants. In this connection, the last-mentioned embodiments of the present invention can avoid or solve a problem with autologous vaccination procedure, namely that autologous tumour cells are poorly immunogenic.

In a specific embodiment of the invention, there is provided an antisense RNA, being antisense to mRNA encoding osteonectin or a functional fragment thereof. In use of the specific embodiment of the invention, administration of this antisense RNA results in (1) reduced osteonectin activity, or (2) reduced amount of secreted osteonectin, or (3) reduction of activity of secreted osteonectin, or (4) otherwise results in a decrease of osteonectin or a decrease in osteonectin activity or a decrease in active osteonectin.

It is observed that cells treated according to the invention are (a) less tumour-like, or (b) less prone to become tumour-like, or (c) able to influence neighbouring tumour cells so that those neighbouring tumour cells become less tumour-like or cease to be tumour cells.

The invention also provides use of an inhibitor of osteonectin in manufacture of a medicament for tumour cell therapy.

A yet further aspect of the invention provides a composition for use in tumour cell therapy, comprising cells that have been transformed with a vector of any of the invention. The composition is conveniently prepared by transforming a cell with a vector of the invention, so that the transformed cell expresses the genetic material of the vector, and formulating the cell in a pharmaceutically acceptable carrier.

Another aspect of the invention provides a pharmaceutical composition, for use in tumour therapy, comprising a compound capable of stimulating a tumour cell to express IL-8, and a pharmaceutically acceptable carrier, and a method of tumour therapy comprising administration of an effective amount of a compound that stimulates a tumour cell to express IL-8.

Another aspect of the invention provides a pharmaceutical composition, for use in tumour therapy, comprising a compound capable of stimulating a tumour cell to express GROα, and a pharmaceutically acceptable carrier, and a method of tumour therapy comprising administration of an effective amount of a compound that stimulates a tumour cell to express GROα.

The invention thus provides inhibition of osteonectin activity in tumour cells or cells that might become tumour cells, in particular cancer cells. Inhibiting osteonectin activity can include preventing secretion of osteonectin, preventing expression of osteonectin, decreasing the activity of expressed osteonectin, administering an inhibitor of osteonectin selected from a compound that binds osteonectin and inhibits its activity and a compound that cleaves or alters or mutates osteonectin and inhibits its activity, an antagonist for an osteonectin receptor, a compound that blocks initiation of osteonectin expression, a compound that interferes with an osteonectin promoter, or a compound that otherwise decreases osteonectin activity.

BRIEF DESCRIPTION OF THE DRAWINGS

The invention is now described in specific embodiments with reference to the accompanying drawings in which.

EXAMPLES

Figure 1:
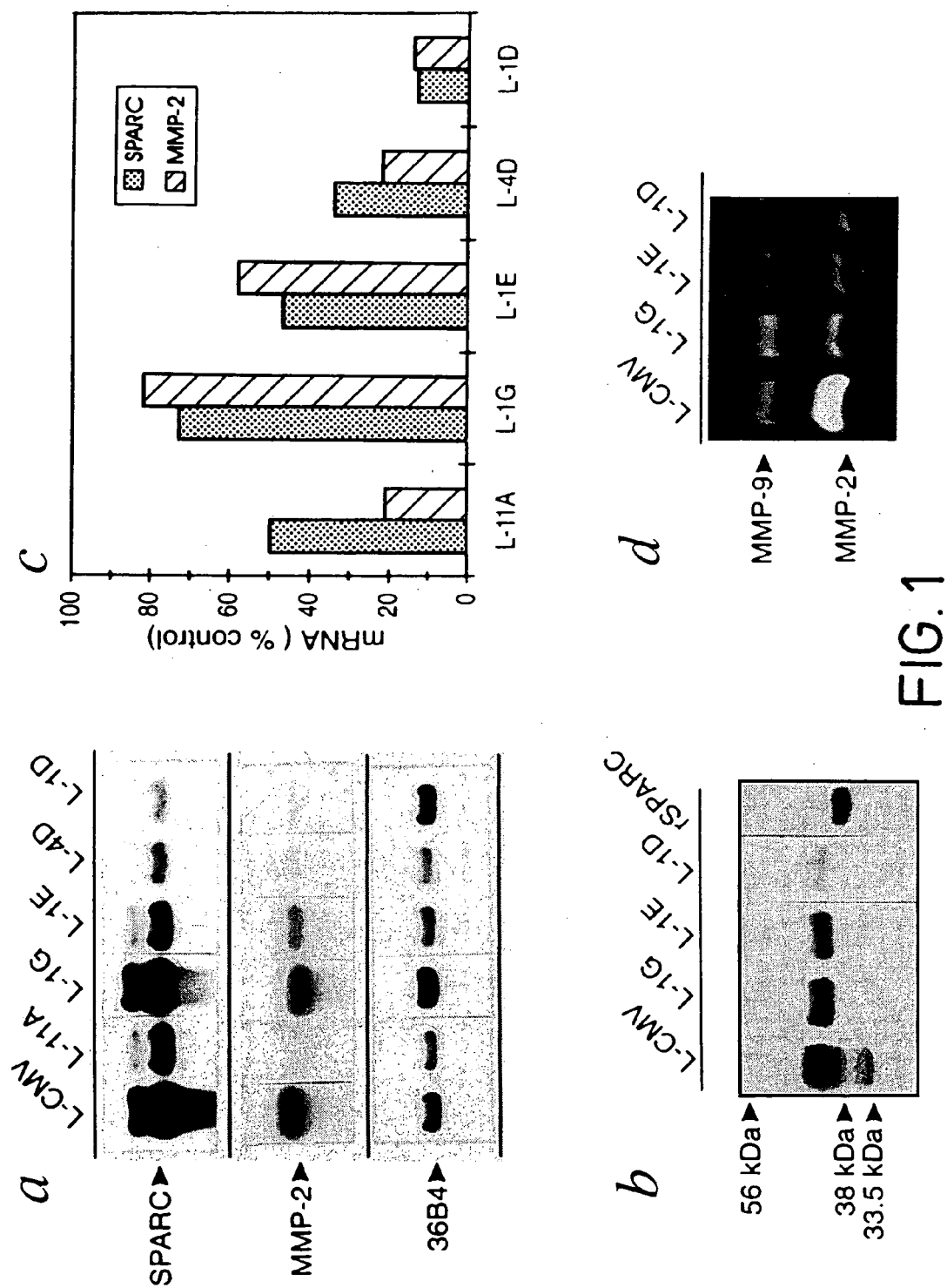
FIG. 1 shows decrease in SPARC and Gelatinase A (72 kDa) levels in IIB-MEL-LES clones transfected with SPARC antisense cDNA. The parts of FIG. 1 indicate a) expression levels of 5 isolated clones including those selected for further studies; b) protein bands from media of L-CMV cells and the different clones, electrophoresis in a minichamber, detected using anti-SPARC IgG; c) comparative mRNA expression of SPARC and Gelatinase A expressed by the different clones; d) zymography of serum-free conditioned media from L-CMV cells and the different clones.

Examples of the invention and materials for use in the invention can be made inter alia with the help of polynucleotides (known per se) encoding osteonectin.

Example 1

Plasmids Encoding Antisense Oligodeoxyribonucleotide to Human Osteonectin:

cDNAs encoding human SPARC (osteonectin), and their cloning, sequence and DNA manipulation have been described for example by:—Manson I J, Taylor A, Williams J G, Sage H, and Hogan B L M, EMBO J. 1986; 5: 1465–1472 'Evidence from molecular cloning that SPARC, a major product of mouse parietal endoderm, is related to an endothelial culture shock glycoprotein of Mr 43,000'— giving sequence data, and incorporated herein by reference; and Swaroop A, Hogan B L M, and Francke U; Genomics 1988; 2: 37–47: 'Molecular Analysis of the cDNA for human SPARC/ osteonectin/ BM-40: sequence, expression and localisation of the gene to chromosome 5q31–q33', also giving sequence data and incorporated herein by reference (SEQ ID NO:1). O L Podhajcer et al have described, in 'Comparative expression of the SPARC and stromelysin-3 genes in mammary tumors', The Breast 5 (1996) pp 13–20 [9], the preparation and cloning of a 1.6 kb DNA sequence encoding full-length human SPARC (osteonectin), and particularly for example its isolation and cloning in known expression vector pET-3b. The cDNA was isolated from a breast cancer cDNA library, and has a coding sequence corresponding to the coding sequence of the cDNA given in FIG. 3 of A Swaroop et al (1988), cited below, and incorporated herein by reference. SPARC (osteonectin) antisense expression is conveniently obtained from a 1.6 kb cDNA for SPARC extending for example from nucleotide 15 to nucleotide 1698 of the sequence given by Swaroop et al (op.cit.), or otherwise as described in reference [9], by excising a clone in the antisense orientation using HindIII and ApaI, and subcloning this product in the same orientation in the HindIII-ApaI sites of the commercially available mammalian expression vector Rc/CMV, driven by the cytomegalovirus promoter (Invitrogen Corp), to create a plasmid designated herein as pCMV/SP-AS.

Reagents useful for carrying out related manipulations are also described in the given references. Osteonectin/SPARC is expressed as a polypeptide when desired e.g. in a bacterial system, in order to raise rabbit antisera against SPARC/osteonectin, as described in reference [9].

An antisense oligodeoxyribonucleotide to SPARC/osteonectin is prepared from the 1.6 kb cDNA encoding SPARC/osteonectin by harvesting the pCMV/SP-AS plasmids mentioned above and digesting with HindIII and ApaI, and is purified using agarose gel.

Melanoma Cells Transfected with Antisense Oligodeoxyribonucleotide to Human Osteonectin:

Melanoma cells are transfected with plasmid pCMV/SP-AS as described above by coprecipitation of the DNA with calcium phosphate. Stable transfectants are selected with geneticin (GIBCO-BRL, 0.5 mg/ml). Isolated clones are obtained by ring cloning and limiting dilution.

Genetically Disabled Herpesviral Vector Encoding Antisense Oligodeoxyribonucleotide to Human Osteonectin:

Antisense DNA to human osteonectin is also used together with techniques as described in specification WO 96/26267 (Cantab Pharmaceuticals Research Limited: Inglis et al) and is adaptable readily to the construction of a genetically disabled herpesviral vector (a gH-deleted defective HSV2 virus vector) encoding antisense oligodeoxyribonucleotide to human osteonectin, as follows:

Antisense oligodeoxyribonucleotide to SPARC (osteonectin) (prepared as described above, by digestion of cloned plasmid pCMV/SP-AS with HindIII and ApaI) is prepared for cloning by (for example) engineering the DNA ends so that the polynucleotide to be inserted, provided with a suitable promoter, and preferably also a poly A signal to facilitate transport of mRNA into the cytoplasm, in per-se known manner, has complementary ends to match (at the 5' end) a HindIII site and (at the 3' end) a EcoRI site.

Manipulations to effect these alterations in the SPARC antisense oligodeoxyribonucleotide are carried out in per-se known manner based on standard procedures described in 'Molecular Cloning: A Laboratory Manual' eds. J Sambrook, E F Fritsch and T Maniatis, 2nd ed 1989, Cold Spring Harbor Laboratory Press.

The polynucleotide is then inserted into a gH-deleted defective HSV2 viral vector by modifying the example description given in specification WO 96/26267. For example, the prepared DNA (oligodeoxyribonucleotide) is ligated into a cloning vector pcDNA3 (available from Invitrogen Corporation) between the HindIII and EcoRI sites, and cloned.

The resulting vector may be designated pcDNA3-hSPARC. This is digested with EcoRI, and then with HindIII, blunt-ended, and cloned into vector pIMC14 as described in specification WO 96/26267 (in place of the murine gene as used in connection with the description given on pages 28–29 of WO 96/26267).

The resulting cloning vector encoding antisense oligodeoxyribonucleotide to osteonectin is then used in adaptations of other procedures described in specification WO 96/26267, including making a gH-deleted defective HSV2 virus vector encoding antisense oligodeoxyribonucleotide to human osteonectin at the site of deletion of the gH gene.

Other techniques for use of antisense polynucleotides, known per se, are readily adaptable to the specificity needed for the present application by using suitable nucleotide sequences, e.g. of at least about 12 nucleotides complementary in sequence to the sequence of the chosen osteonectin target; by choosing from among known promoters suitable to the cellular environment in which they are to be effective, and other measures known per se. For example, the sequence at the 5' end of the coding sequence of the cDNA given in the Swaroop et al (1988) paper cited above can be used alternatively or in addition to derive antisense sequences for blocking purposes as described herein.

Reference is made to further techniques for use of antisense RNA to disrupt expression of a target gene, as for example indicated (in connection with a sialidase gene) in specification WO 94/26908 (Genentech: TG Warner et al). Techniques for using antisense oligonucleotides capable of binding specifically to mRNA molecules are also indicated in specification WO 94/29342 (La Jolla Cancer Research Foundation and the Regents of the University of Michigan: R Sawada et al) (in particular connection with mRNA encoding human lamp-derived polypeptides). Techniques for antisense oligonucleotides complementary to target RNA are indicated in specification WO 94/29444 (Department of Health and Human Services: B Ensoli and R Gallo) (as applied to basic fibroblast growth factor RNA). Techniques for using antisense oligonucleotides having a sequence substantially complementary to an mRNA which is in turn complementary to a target nucleic acid, in order to inhibit the function or expression of the target, are indicated in WO 94/24864 (General Hospital Corporation: H E Blum et al), (as applied to inhibition of hepatitis B viral replication). A review of antisense techniques is given by D Mercola and J S Cohen, ch. 7 pp 77–89 in in R E Sobol and K J Scanlon (eds.) 'Internet Book of Gene Therapy: Cancer Therapeutics' (Appleton & Lange, Stamford, Conn., 1995). Applications to other target specificities are accessible by adaptation.

Techniques for using ribozymes to disrupt gene expression are also known per se. For example, techniques for making and administering ribozymes (or antisense oligonucleotides) in order to cleave a target mRNA or otherwise disrupt the expression of a target gene are indicated in specification WO 94/13793 (Apollon: C J Pachuk et al) (as applied to ribozymes that target certain mRNAs relevant to leukemias). A review of ribozyme techniques is given in M Kashani-Sabet and K J Scanlon, ch. 8 pp 91–101 in R E Sobol and K J Scanlon (eds.) 'Internet Book of Gene Therapy: Cancer Therapeutics' (Appleton & Lange, Stamford, Conn., 1995). Here also, applications to other target specificities are readily accessible by adaptation. According to examples of the invention, antisense oligonucleotide technique can be used together with ribozyme technique to disrupt the expression of osteonectin in a target cell, and the corresponding nucleic acid can be delivered in any appropriate viral or non-viral vector, or as naked DNA. If desired, expression of more than one gene can simultaneously be blocked by including suitable antisense sequences.

Characteristics of Human Melanoma Cell Lines Used for Study and Demonstration:

Studies were carried out to compare the in vitro invasive capacity of different human melanoma cell lines [12]. In three different experiments, IIB-MEL-LES cells exhibited 5 to 10-fold higher capacity to traverse matrigel, compared with the other cell lines (IIB-MEL-LES: 50.5 +/−8.4. IIB-MEL-IAN: 10.3+/−1.1 and IIB-MEL-J: 4.8+/−1.1 cells/field: mean+/−SD).

In another series of experiments, nude mice were xenografted with $2\times10^6$–$10\times10^6$ cells corresponding to each cell line and tumour growth was followed. Starting from $3\times10^6$ cells, tumour growth was observed in 100% of mice injected with every melanoma cell line. Yet, differences in tumour growth rate were observed among the three cell lines. When $3\times10^6$ cells were injected, a mean tumour volume of 0.1 cm$^3$ was observed after 34+/−3.3 days (mean+/−SD), 42.5+/−6.5 days and 51.5+/−5.7 days in mice injected with IIB-MEL-LES, IIB-MEL-IAN and IIB-MEL-J cells, respectively. Similarly, a mean tumour volume of 1 cm^3 was reached after 46.6+/−4.2 days, 68.4+/−6.4 days and >80 days in mice injected with IIB-MEL-LES, IIB-MEL-IAN and IIB-MEL-J cells, respectively.

Downregulation of SPARC Expression:

Twelve clones derived from the most aggressive IIB-MEL-LES cell line and 16 from the less aggressive IIB-MEL-IAN cell line were analyzed for SPARC mRNA expression following SPARC antisense c-DNA transfection. Three IIB-MEL-LES-derived clones were selected (termed L-1G, L-1E and LID) exhibiting 27%, 52% and 87% decrease in SPARC mRNA expression compared to L-CMV cells transfected with the vector alone (FIG. 1a). Similarly, 4 IIB-MEL-IAN-derived clones (termed I-1H. I-1N, I-1V) exhibiting 73%. 82%. 66% and 61% decrease in SPARC mRNA expression compared to I-CMV control cells were also selected (not shown).

SPARC produced by different normal cells migrates as a single band with an apparent Mr of 40–43 kDa [5,6]. In contrast, IIB-MEL-LES and IIB-MEL-IAN cells, as well as fresh melanoma samples, produced up to three additional protein species as a result of post-translational cleavage by a leupeptin-inhibitable protease (M. F. L. et al., submitted, and FIG. 1b). Western analysis revealed the complete disappearance of the low molecular weight bands in the three IIB-MEL-LES derived clones, and a gradual decrease in the major band expression levels (FIG. 1b). Parental and L-CMV cells secreted 0.13–0.2 ug/ml/$10^6$ cells of SPARC. Clones L-IG, L-1E and L-1D secreted 0.07–0.08, 0.05–0.03 and 0.03–0.01 ug/ml/$10^6$ of SPARC, corresponding to an average decrease in SPARC secretion of 54%. 76.5% and 88.5% respectively.

In vitro growth and invasive capacity of transfectants: FIG. 2a shows the in vitro growth properties of the different IIB-MEL-LES transfectants. When plated at low cell density ($1\times10^4$ cells per well of a 24-well plate) a slight delay in the onset of logarithmic growth of SPARC antisense-transfected clones was observed, compared to L-CMV cells. Once the different cell types reached the logarithmic phase no difference in their doubling time was observed. Cells plated at higher density ($2×10^4$ and $4×10^4$ cells per well of a 24-well plate) showed no difference compared to L-CMV cells (not shown).

When the transfectants were further analyzed for their capacity to invade matrigel-coated membranes we found that clones L-1 G and L-1 E exhibited in average almost 70–80% reduction in their invasive ability, while clone L-1D was essentially non-invasive (FIG. 2b). Similarly clones I-1H, I-1N, I-1T and I-1V exhibited 55%, 88%, 88% and 81% reduction respectively in their in vitro invasive capacity compared to I-CMV cells.

Gelatinase A and the in vitro invasiveness of melanoma cells: Initial zymographic analysis of serum-free conditioned media obtained from the different cell lines demonstrated that the higher in vitro invasive capacity of IIB-MEL-LES cells correlated with gelatinase A (MMP-2) activity and protein levels (FIGS. 3a and 3b). In addition, an antisera anti-gelatinase A which completely blocked its gelatinolytic activity (FIG. 3c) inhibited almost 50% IIB-MEL-LES cells invasive capacity. In view of the correlation between gelatinase A levels and the in vitro invasive capacity of IIB-MEL-LES cells, we studied gelatinase A levels in the different IIB-MEL-LES derived clones. FIGS. 1a and 1c show a decrease in the expression levels of gelatinase A mRNA following the down-regulation of SPARC mRNA levels in the different IIB-MEL-LES derived clones, which was accompanied by a decreased gelatinase A activity (FIG. 1d).

Cell adhesion to Matrigel and migration: Tumour cell attachment to surrounding matrix is the initial step leading to pericullular matrix degradation. Similarly, tumour cell attachment to matrigel must precede invasion. We found that the 3 IIB-MEL-LES derived clones displayed a reduced capacity to adhere to matrigel, suggesting that the decrease in their in vitro invasive capacity may be associated, at least in part, with a diminished adhesion capacity (FIG. 2c). Interestingly, all the 4 IIB-MEL-IAN-derived clones also showed a strong reduction in their ability to adhere to matrigel and 3 of them essentially did not adhere (I-1H: 50%, I-1T: 0%, I-1V 0% and I-1N 8% compared to I-CMV control cells). In addition, we found a slight but statistically significant inhibition in the in vitro chemokinetic migration of the three IIB-MEL-LES-derived clones compared to L-CMV cells (FIG. 2d).

In vivo tumorigenicity: The in vitro data prompted us to study whether decreased SPARC expression levels might affect melanoma cells tumorigenicity. Table X demonstrates tumour formation in all mice xenografted with L-CMV cells in two independent experiments. All mice injected with cells obtained from the 3 IIB-MEL-LES derived clones showed no sign of tumour formation, even after eight months (Table X). Histologic analysis of L-1D injection site 24 hr after injection showed a statistically significant increase in the recruitment of segmented neutrophils compared to L-CMV injection site (FIG. 4a), and a massive tumour cell necrosis (not shown). After 72 hr, the L-1D injection site was still infiltrated by a significant number of segmented neutrophils (FIGS. 4a and 4b) while only few neutrophils were visible in the L-CMV injection site (FIGS. 4a and 4c). After 7 days, the LES-1D injection site showed no viable tumour cells (not shown). A similar increased recruitment of segmented neutrophils was observed at the site of injection of I-1T and I-1N cells compared with I-CMV cells. In the case of I-1N cells we found no viable tumour cells at the injection site after 72 hr, while the absence of viable cells at the injection site of I-1T cells was evident after 7 days (not shown).

Further methods useful in the performance of the invention are as follows:

Cell Lines: The IIB-MEL-J, IIB-MEL-LES and IIB-MEL-IAN cells lines were established from metastatic melanomas and were routinely grown in melanoma medium without tranferrin and epidermal growth factor [12]. HFL-1 human fibroblasts (ATCC, CCL153) were grown in DMEM, 10% FBS and antibiotics. Cultures were maintained at 37 degC in a 5% $CO_2$ humidified incubator.

SPARC antisense expression: A 1.6 kb full length cDNA encoding for human SPARC extending from nucleotides 15–1698 was isolated and clones as described [9]. A clone in the antisense orientation was excised with Hind III and Apa I and subcloned in the same orientation in the Hind III-Apa I sites of the mammalian expression vector Rc/CMV driven by the cytomegalovirus promoter (Invitrogen), to create plasmid pCMV/SP-AS. Melanoma cells were transfected with pCMV/SP-AS by coprecipitation of the DNA with calcium phosphate. Stable transfectants were selected with geneticin (GIBCO-BRL, 0.5 mg/ml). Isolated clones were obtained by ring cloning and limiting dilution.

Preparation of SPARC antiserum, western and ELISA studies: A full length cDNA for human SPARC was subcloned into the expression vector pET-3b as described [9]. BL-21 cells transformed with pET-3b plasmid or with pET-3b/SPARC plasmid were grown and induced by 1 mM IPTG. The bacterial soluble fraction containing recombinant SPARC was concentrated by adding ammonium sulphate to 80% saturation. After centrifugation, the pellet was resuspended in lysis buffer containing 6M urea, loaded on a DEAE Sephacel column (Pharmacia, Sweden) followed by protein elution with a discontinuous NaCl gradient. SPARC eluted at 200 mM NaCl concentration was dialyzed against PBS containing gradually decreasing concentrations of urea until it was completely removed. This sample was used to raise a rabbit antiserum by standard procedures [36]. The Protein G Sepharose-affinity purified-IgG fraction (Pharmacia, Sweden) recognized one band of 42 kDa in serum-free conditioned medium of HFL-1 cells corresponding to the expected Mr of SPARC and did not react with serum-free conditioned media of the human breast cancer cell lines MCF-7 and MDA-MB-231 which did not express SPARC mRNA (M. F. L. et al., submitted).

Nearly confluent human melanoma cells were washed twice with PBS and kept in serum-free medium. After 24 hr the medium was collected, centrifuged for 10 min at 1,500 rpm to remove debris and concentrated with ammonium sulfate. The precipitate was dissolved in PBS in the presence of protease inhibitors (PMSF and EDTA, 1 mM final concentration) and dialyzed against the same buffer. Samples were separated by reduced SDS-PAGE and transferred onto nitrocellulose membranes. After blocking with skimmed milk in PBS, membranes were incubated overnight at 4 degc with affinity purified antiserum raised against human rSPARC (at 1/1000 dilution) or rabbit antiserum anti-human gelatinases. After washing with 0.05% Tween-20 in PBS, the membranes were further incubated for 2 hr at room temperature with alkaline phosphatase-labelled goat anti-rabbit IgG (Jackson Immuno Research). Bands were detected using NBT-BCIP following manufacturer's instructions (GIBCO-BRL).

For ELISA studies, 30 ul per well of concentrated conditioned media was seeded in duplicate in 96-well-polyvinyl ELISA plates and dried overnight at 37 degC. Non specific binding was blocked with 5% skimmed milk over 2 hr at room temperature and samples were incubated overnight at 4 degC with anti-SPARC antiserum (at 1/250 dilution). After washing with 0.1% BSA-BPS, SPARC was detected using a peroxidase-conjugated swine Ig anti-rabbit 1 g (Dako). After washing, the reaction was developed with o-phenylenediamine and the absorbance read at 415 nm. The results were obtained from a standard curve with purified rSPARC (range 0–50 ug/ml). Three experiments using different batches of conditioned media were performed.

Zymography: Analysis of gelatinolytic activity was performed using 10% SDS-PAGE gels containing 0.1% gelatin. One part of serum-free conditioned media obtained as described was mixed with 1 part of Laemmli's buffer (without beta-mercaptoethanol) and incubated for 30 min at room temperature before loading in the gel. At the end of the electrophoresis, the gels were washed 30 min each at room temperature, with the following solutions: a) 50 mM Tris-HCl, pH 7.5, 2.5% Triton X-100; b) 50 mM Tris-HCl, pH 7.5, 2.5% Triton X-100, 5 mM CaCl2, 1 uM ZnCl2. C) 50 mM Tris-HCl, pH 7.5, 5 mM CaCl2, 1 uM ZnCl2, followed by an overnight incubation at 37 degc in 50 mM Tris-HCl, pH 7.5, 5 mM CaCl2, 1 uM ZnCl2. After staining with Coomassie Brilliant Blue R-250, gels were destained and photographed.

When the effect of the antisera against gelatinases was tested, conditioned media was preincubated during 45 min at room temperature with the antiserum before loading in the gel [37].

Invasion, adhesion and migration assays: The invasiveness of parental and transfected cells was determined in 24-transwell chambers (Costar). PVP-free polycarbonate filters, 8-um pore size, were coated with 5 ug of Matrigel and dried under a hood. After adding 600 ul of medium (DMEM: 0.1% BSA) in a cluster plate well, coated transwells were mounted in the chamber. Cells were collected with a short exposure to citrate buffer (0.13 M sodium citrate and 0.015 M KCl), washed with PBS, resuspended at $1 \times 10^6$ cells/ml in DMEM:0.1% BSA buffer, and 0.1 ml were added to the inside of the transwell. After 16–18 hr incubation at 37 deg C. in 5% $CO_2$, the cells on the upper face of the filter were removed with a cotton swab. Cells attached to the lower face of the filters were fixed in methanol, stained with hematoxylin and counted. To test the involvement of gelatinases, invasion assays were performed in the presence of different dilutions of anti-gelatinase antisera. The migration assays were performed in a similar way without materiel coating, after soaking polycarbonate filters in gelatin to increase cell adhesion to the filters [38]. Serum free-conditioned media obtained from HFL-1 fibroblasts was used as chemoattractant.

For adhesion assays, the plastic surface of 96-well microtiter plates was coated with 5 ug of matrigel and dried under a hood. Cells collected with citrate buffer were washed with PBS, resuspended at $2.5 \times 10^5$ cells/ml in DMEM and 100 ul added to each well. At different times well plates were washed with PBS to removed unattached cells and fixed with paraformaldeyde. Ten random fields/wells were counted under phase contrast microscopy. Each experiment was performed at least in triplicate.

Table X shows in-vivo tumorigenic capacity of IIB-MEL-LES cell clones with stable expression of SPARC antisense RNA. 8–12 week old, male athymic balb/c nu/nu mice received into the left flank s.c. injections of $3 \times 10^6$ cells, in a total volume of 0.1 ml. Tumor volume was measured in the two perpendicular diameters with calipers. Mice were obtained from the National Commission of Atomic Energy, Buenos Aires. Experiments 1 and 2 were terminated after 240 and 210 days respectively. The data are expressed as the number of mice which developed tumors of 1.5 $cm^3$, of total mice.

| | Control | Cell Clones | | |
|---|---|---|---|---|
| | L-CMV | L-1G | L-1E | L-1D |
| Experiment 1 | 6/6 | 0/6 | 0/6 | 0/6 |
| Experiment 2 | 7/7 | 0/7 | 0/7 | 0/7 |

Further results are shown in accompanying FIGS. 1–4:—

FIG. 1 indicates decrease in SPARC and Gelatinase A (72 kDa) levels in IIB-MEL-LES clones transfected with SPARC antisense cDNA. a) 10 ug of total RNA were electrophoresed in 1% agarose gels in the presence of formaldeyde, blotted into nylon membranes and hybridized with probes corresponding to SPARC and 36B4 [9]. The nylon membrane was washed and re-hybridized with a probe corresponding to gelatinase A probe extending from nucleotides 142 to 2150 [39]. Autoradiography was for 24 hr for SPARC and 36B4 and 96 hr for gelatinase A. Only the expression levels of 5 isolated clones are shown, including those selected for further studies. b) 15 ug of total protein obtained from serum-free conditioned media of L-CMV cells and the different clones was loaded in each lane and electrophoresed in a minichamber. Protein bands were detected using affinity purified anti-SPARC IgG. Molecular weight markers are indicated in the left. c) Comparative mRNA expression of SPARC and Gelatinase A expressed by the different clones after quantification by two-dimensional densitometric scanning with an ULTROSCAN XL densitometer (Pharmacia, Sweden) and normalized by dividing by the 36B4 signal for each sample. d) Zymography at neutral pH of serum-free conditioned media obtained from L-CMV cells and the different clones. The migration of the 72 kDa nad the 92 kDa gelatinases is shown.

Figure 2:
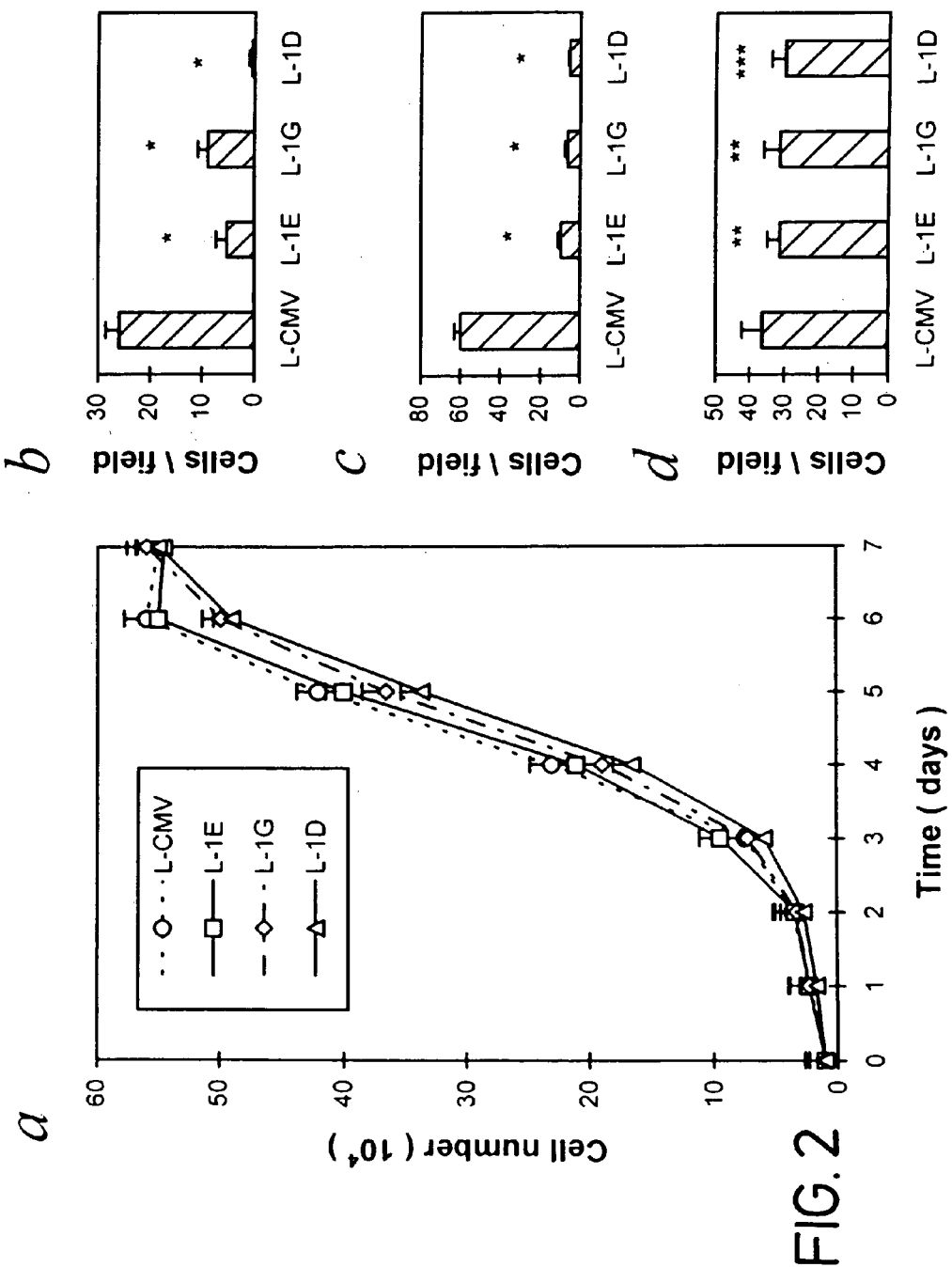
FIG. 2 shows in vitro features of IIB-MEL-LES clones transfected with SPARC antisense cDNA: a) cell growth, cell counts, in vitro invasiveness (b), adhesiveness (c), and migration (d).

FIG. 2 shows in-vitro features of IIB-MEL-LES clones transfected with SPARC antisense cDNA. a) cells were trypsinized, washed and $1 \times 10^4$ cells plated in each well of 24-well plates in triplicates in medium without selecting drug. Cell growth was followed until cells detached from the plastic. Cell counts were performed with a hemocytometer. Cells corresponding to each of the selected clones and L-CMV cells were studied for in vitro invasiveness (b), adhesiveness (c), and migration (d). The experimental details are described in methods section. The significance of differences was determined using the One Way Analysis of Variance (ANOVA) and Tukey-Kramer Multiple Comparison Tests, p<0.001 (*); p<0.01 (); p<0.05 (*)

Figure 3:
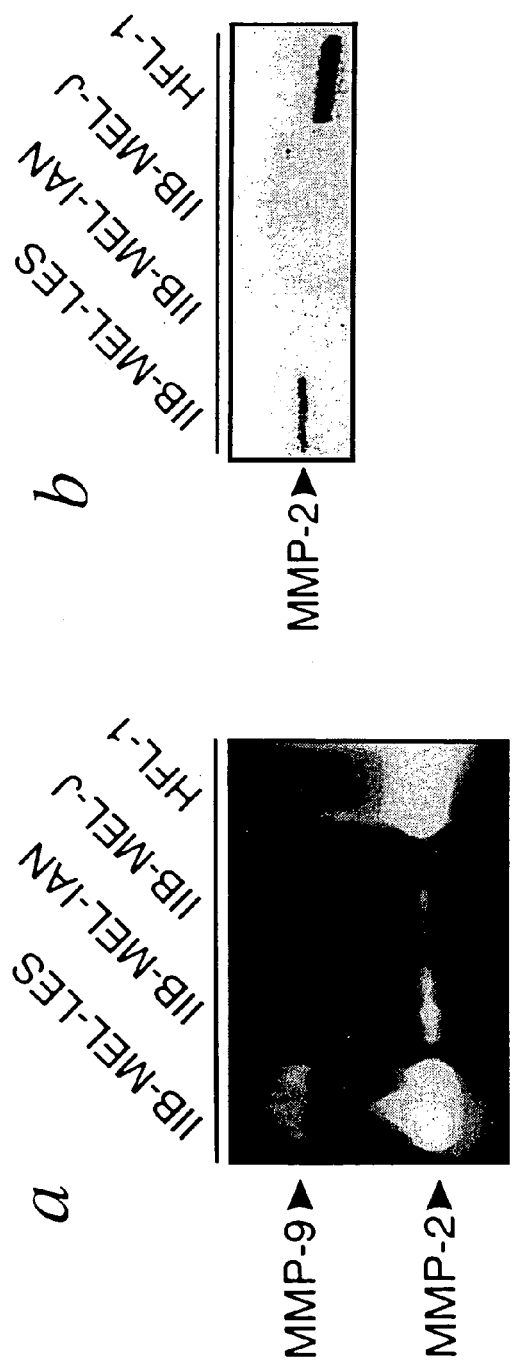
FIG. 3 shows gelatinase A expression in human melanoma cell lines. Gelatinolytic activity (a) and western analysis (b) of serum-free conditioned media from different cell lines; c) gelatinolytic activity of IIB-MEL-LES-serum free-conditioned media under various conditions.
Figure 3:
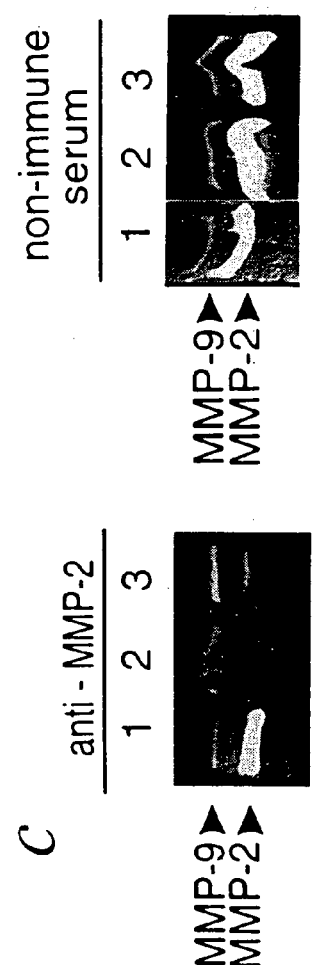

FIG. 3 shows gelatinase A expression in human melanoma cell lines. Gelatinolytic activity (a) and western analysis (b) of serum-free conditioned media obtained from different cell lines; c) gelatinolytic activity of IIB-MEL-LES-serum free-conditioned media in the presence of 72 kDa antiserum: 1) no serum added; 2) 1/50 dilution of 72 kDa antiserum; 3) 1/100 dilution of 72 kDa antiserum. See methods section for details.

Figure 4:
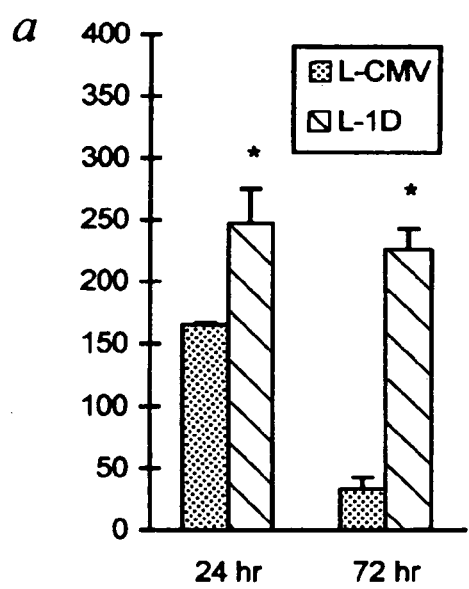
FIG. 4 shows analysis and quantification of neutrophil infiltrate at injection sites of tumor cells in nude mice.
Figure 4:
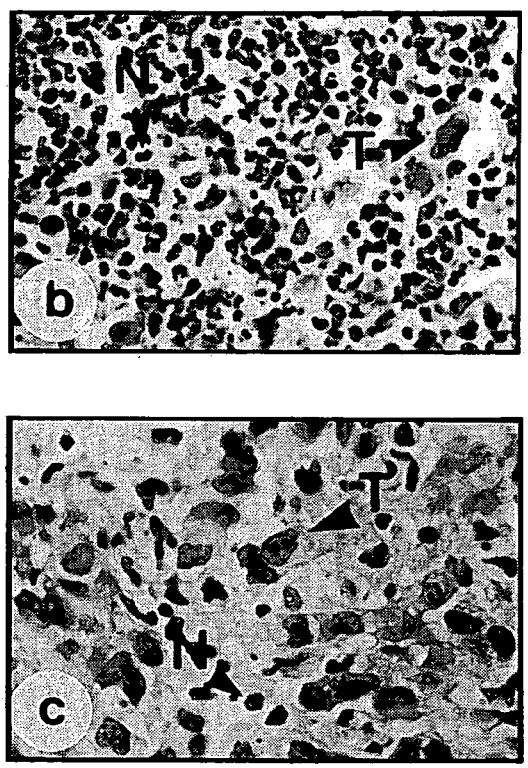

FIG. 4 shows analysis and quantification of the neutrophil infiltrate at the injection sites of tumor cells in nude mice. Cells were injected in the left flank of nude mice. The site of injection was removed after 24 hr and 72 hr, paraffin-embedded, cut and stained. a) 5–10 different fields corresponding to microphotographs (at 1000× magnification) were used for calculating the neutrophil infiltrate. Data represent the means+/−s.d (bars): p<0.001. b) Microphotographs showing the site of injection after 72 hr of: b) L-1D cells: c) L-CMV cells; N: segmented neutrophils; T: tumor cells.

It has also been found, in accordance with the invention, that L-1D cells in which SPARC/osteonectin has been downregulated in accordance with the description herein, abrogate tumour growth of parental cells, for example when xenografted into nude mice as mixed cells in doses of about $3 \times 10^6$ parental cells, using ratios of cell numbers of the respective types of up to e.g. 4:1 (parental cells:L-1D cells) and following tumour outcome for 4 months.

Example 2

We have shown above that downregulation of SPARC expression in human melanoma cells completely prevented tumor formation in mice. This effect was accompanied by a localized and massive recruitment of PMNLs which were probably responsible for tumor cell rejection. In the work described below we use coinoculation of these genetically modified cells with parental cells to induce an in vivo dominant bystander effect leading to the elimination of parental cells. Pronounced infiltration of PMNLs is seen in regressing tumors. Moreover, in vitro studies with human blood cells show that SPARC downregulation is associated with human melanoma cells overproduction of IL-8 and GROα and increased PMNLs chemotaxis and activation.

Methods

Cells and Cell Cultures

SPARC antisense transfected clones L-1G, L-1E and L-1D, and parental IIB-MEL-LES cells transfected with the vector alone (L-CMV) were routinely grown in RPMI 1640 (Gibco BRL, Grand Island, N.Y.) containing 5 ng/ml insulin (Sigma, St. Louis, Mo.) 40 ug/ml Gentamicin and 10% FCS (Gibco BRL, Grand Island, N.Y.) at 37° C. in a 5% $CO_2$ humidified incubator.

Polymorphonuclear Leukocytes (PMNLs) Isolation

Venous blood from healthy human volunteers was collected into 3.4 U/ml heparin and acid citrate dextrose (0.73% citric acid/2.2% sodium citrate.$2H_2O$/2.45% dextrose. $H_2O$) 0.8 ml /10 ml of blood. Red cells were separated by sedimentation with 6% dextran saline solution (1 part to 5 of blood) and the leukocyte-rich plasma was harvested. The leukocytes were sedimented (150×g, 10 min. at room temperature) and resuspended in $Ca^{2+}$, $Mg^{2+}$-free Tyrode's solution (T1−) containing 5% autologous platelet-poor plasma (PPP), for $^{51}Cr$ labeling or it was resuspended in T1− with 10% PPP. Two Percoll cushions of 2.5 ml each containing 77% Percoll at the bottom followed by 62% (based on 100%=isotonic Percoll), were layered in a 15 ml conical polypropylene tube. Density gradient centrifugation was performed at 200×g (15 min at room temperature) in a swinging bucket rotor. Two bands were obtained, harvested, and washed once with T1−. The PMNLs fraction was recovered at the 62–77% Percoll interphase yielding 1–2× $10^6$ PMNLs from 1 ml of starting blood with >90% purity and >95% viability by crystal violet staining and trypan blue exclusion.

$^{51}Cr$ labeling of leukocytes—Leukocytes were labeled with $^{51}CrO_4K_2$ (25 µCi/ml) by incubation for 30 minutes at 37° C. Labeled leukocytes were washed once with T1−, and resuspended in T1−/PPP 10%.

Endothelial Cell Cultures

Human umbilical vein endothelial cells (HUVE) were isolated and cultured in flasks as described by Jaffe (1973). Briefly, endothelial cells were isolated from umbilical cords after treatment with 0.5 mg/ml collagenase (Sigma), in 0.01M PBS, pH 7.4, and grown in RPMI 1640, containing 2 mM L-Glu, 2-mercaptoethanol, sodium pyruvate, penicillin G/streptomycin and supplemented with 20% FCS, 25 µg/ml endothelial cell growth supplement (Collaborative Research, Lexington, Mass.), and 45 µg/ml heparin (Sigma Co). Cells were cultured in gelatin-coated culture flasks (Nunc). The HUVE were detached using 0.025% trypsin/ 0.01% EDTA and cultured on gelatin-coated 96 well plates. The HUVE monolayers were used for adhesion studies.

Migration, Adhesion and PMNLs Degranulation Assays

PMNLs migration was determined in 6.5 mm insert chambers (Transwell, Costar, Cambridge, Mass.). 600 µl of serum free-cell conditioned media in 0.5% human serum albumin (HSA) (University of Cordoba hemoderivatives, Córdoba, Argentina) were added to each well and polyvinyipyrrolidone (PVP)-free polycarbonate filter transwells, 3 µm pore size, containing 100/1 of PMNLs at $1.25 \times 10^6$ cells/ml in RPMI 1640/0.5% HSA were mounted in the chambers. After an incubation period of 45 min. at 37° C. and 5% $CO_2$, in an humidified incubator, the transwells were collected and the number of migrated cells was determined by absolute flow cytometry using a Cytoron Absolute (Ortho Diagnostic Systems, Raritan, N.J.) with the Research program. For tumor cell induced migration, $8 \times 10^4$ melanoma cells per ml were seeded in 24-wells culture plate. After 20 hr incubation at 37° C. and 5% $CO_2$, in an humidified incubator, the culture media was discarded and 600 µl of RPMI/HSA was added to each well. PVP-free polycarbonate filter transwells, 3 µm pore size, containing 100 µl of $^{51}Cr$ labeled PMNLs at $1.25 \times 10^6$ cells/ml in RPMI/HSA were placed in the chambers. After 2 hr incubation, the transwells were collected and the number of migrated cells was determined from the $^{51}Cr$ present in each well. For migration blocking experiments, cell conditioned media was incubated at 37° C. for 30 min. with 10/g/ml mouse anti-hIL-8 mAb (6214.11, R&D Systems) or mouse anti-hGROα mAb (20326.1, R&D Systems). We used RPMI/HSA 0.5% as a negative control (spontaneous migration) and 10 nM FMLP in RPMI/HSA 0.5% as a positive control. Because the number of migrated cells vary between leukocyte donors, the results are expressed as a ratio between the number of cells migrating in each sample compared to the spontaneous migration. This ratio is referred to as chemotactic index (CI).

For studying PMNLs adhesion to melanoma cells, 50 µl of $^{51}Cr$ labeled PMNLs was added onto melanoma cell monolayers in 96-well flat-bottom plates containing 50 µl RPMI/HSA 0.5%. After 45 minutes at 37° C., the monolayers were washed 4 times with PBS/Ca2+/Mg2+ and the amount of radioactivity remaining in each well was counted.

Myeloperoxidase release from PMNLs was assessed as an index of degranulation. 50 µl of PMNLs ($10^7$ cells per ml) in T1−/Ca2+/Mg2+, were incubated for 5 minutes with 5 µg/ml cytochalasin B (Sigma Co). Thereafter, 50 µl of conditioned media obtained from the different cell types was added and incubated for additional 30 minutes at 37° C. After centrifugation, 50 µl of supernatants were incubated with OPD substrate and the enzymatic reaction kinetic was measured in a plate spectrophotometer at 450 nm. Because the enzymatic activity vary thoroughly between leukocytes donors, the results are expressed as a ratio between the enzymatic activity induced by each sample and the negative control, which reflects spontaneous myeloperoxidase release. This ratio is referred to as degranulation index (DI).

ELISA Assays

Ninety six wells-ELISA plates (MaxiSorp, Nunc) were coated overnight at 4° C. either with 1 µg/ml mouse anti-hIL-8 mAb or 5 µg/ml mouse anti-hGROα mAb in PBS. For immunochemical development we used the following reagents: either goat anti-hIL-8 mAb (R&D Systems) or goat anti-hGROα mAb (R&D Systems) followed by biotin-labeled donkey anti-goat IgG (Gibco BRL) and streptavidin-conjugated HRP (Gibco BRL). The plates were incubated with OPD until colour developed and the optical density at 492 nm was determined.

Adhesion Assays

For adhesion assays, the plastic surface of 96-well microtiter plates was coated with 5 µg of Matrigel, dried under a hood, and reconstituted with serum-free media. Cells collected with citrate buffer were washed with PBS, resuspended at $2.5 \times 10^5$ cells/ml in DMEM, and 100 µl added to each well. At different times, well plates were washed with PBS to remove unattached cells and fixed with paraformaldehyde. Ten random fields/well were counted under phase contrast microscopy. Each experiment was performed at least in triplicate.

For evaluating βgalactosidase activity, unattached cells were removed and plated on plastic dishes. Twenty four hr later βgalactosidase activity was determined as described [Morling and Russel 1995].

In Vivo Studies

Mice were given s.c. injections into the right flank of a tumorigenic inocula of $4.5 \times 10^6$ parental or genetically modified human melanoma cells, in a total volume of 0.1 ml. Tumor growth was evaluated by measuring the two perpendicular diameters with calipers. In experiments including cells co-injection, the amount of parental cells or parental cells tagged with the β-galactosidase gene was kept at $4.5 \times 10^6$ cells.

Statistical Analysis

Experimental data was analyzed by two-way ANOVA and p-value were estimated by Tuckey HSA post-hoc test. Results were expressed as mean±SEM; 3–9 experiments were performed in each case.

Results

Inhibition of In Vivo Human Melanoma Cell Growth Following Co-Inoculation with Human Melanoma Cells Expressing Reduced Levels of SPARC Experiments were carried out to determine whether SPARC antisense RNA transfected cells may exert a dominant effect capable of affecting parental cell growth. In order to differentiate between parental cells and SPARC antisense RNA transfected cells, we tagged parental cells by transfection with a vector expressing the bacterial β-galactosidase (L-βgal) gene. Initial studies showed no difference in the in vitro growth of L-βgal cells compared to parental cells (not shown). Then, we performed a series of experiments to establish whether SPARC antisense transfectants may impair the in vitro behaviour of L-βgal or parental IIB-MEL-LES cells. No effect was observed on the in vitro growth of the different cell types when cells were co-cultivated in plastic dishes, nor when one cell type was grown in the presence of conditioned media obtained from the other cell type (not shown). Moreover, no significant differences were found when the in vitro adhesion capacity of L-βgal cells was tested in the presence of L-1D cells or their conditioned media (Tables 1 and 2).

In order to evaluate the mechanisms associated with tumor cell rejection following SPARC down-regulation we performed different in vivo experiments. We found no difference in the tumor growth kinetics of L-βgal cells in nude mice compared to parental non modified cells (not shown). However, when mice were xenografted with a 1:1 mixture of L-βgal and L-1D cells no tumor growth was observed. A second experiment using parental non-modified cells instead of L-βgal cells, and different amounts of L-1D cells (at 1:1, 3:2 and 4:1 ratio) gave similar results, and no tumor growth was observed (Table 3). The effect at the lower ratio of L-1D cells was further confirmed in a third experiment.

CXC Chemokines Production by Melanoma Cells

The lack of tumor growth following co-injection of parental cells with SPARC antisense RNA transfected cells suggested that the down regulation of SPARC induces a dominant "bystander" effect leading to the elimination of parental cells expressing SPARC. Since experiments of co-cultivation demonstrated no direct effect of SPARC antisense RNA transfected cells on the in vitro growth and adhesive capacity of parental cells, we hypothesized that this "bystander" effect must involve an intermediate compound produced by SPARC antisense RNA transfected cells which by inducing leukocytes recruitment can lead to tumor rejection.

Figure 5:
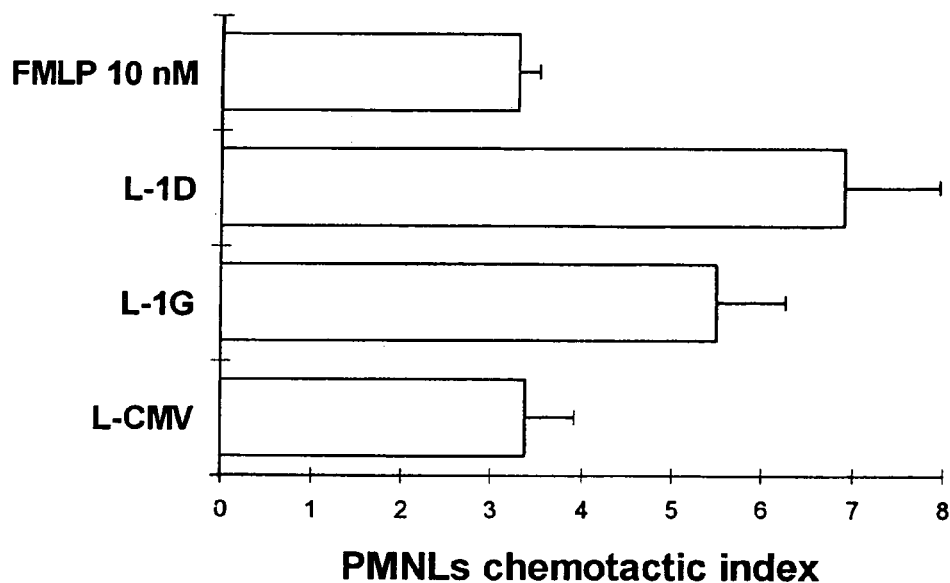
FIG. 5 shows production of PMNLs chemoattractants by melanoma cells. Representative experiments of PMNLs chemotaxis induced by melanoma cells (a), and sequential dilution of L-CMV and L-1G serum 3 culture supernatants (b).
Figure 5:
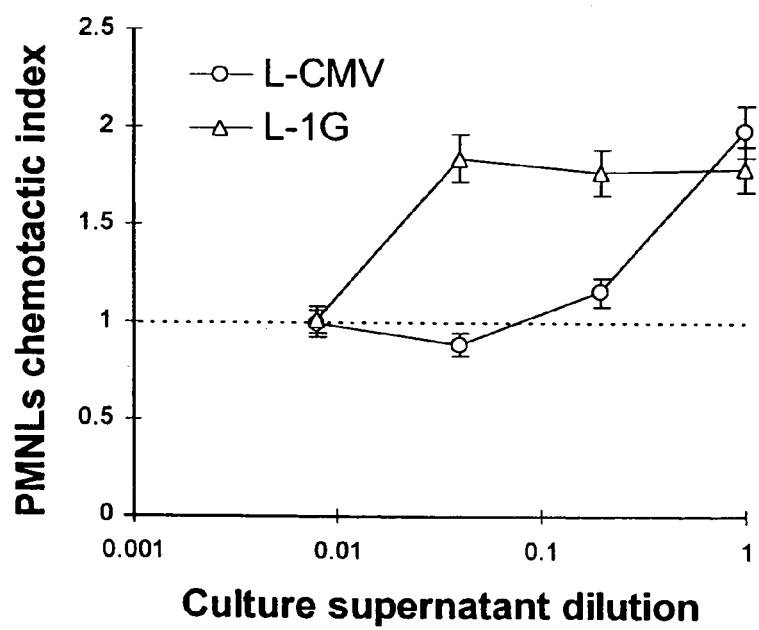

Initially, we tested the production of chemotactic factors by melanoma cells. We determined the chemotactic activity of L-CMV, L-1G and L-1D cell conditioned media (CCM). L-CMV induced 7.1±1.6 fold increase in human PMNLs migration compared to random chemokinetic migration (p<0.0001). This migration was chemotactic rather than chemokinetic, since it could be inhibited by adding CCM to the upper chamber of the transwells (data not shown). Interestingly, L-1G CCM induced 1.8±0.07 fold increase in PMNLs migration compared to L-CMV (FIG. 5a, p<0.001). Parallel experiments demonstrated that also L-1D CCM induced 2-fold increase in PMNLs chemotaxis compared to L-CMV cells (FIG. 5a). Similar results were obtained when melanoma cells were used as a direct source of chemotactic stimulus rather than their CCM and when murine PMNLs were used instead of human PMNLs (not shown). No significant difference was observed in the chemokinetic migration of mononuclear cells induced by L-1G and L-1D CCM compared to L-CMV CCM. According to the initial studies showing similar effects on murine and human PMNLs we decided to continue the work with cells obtained from human donors.

Since the dose-response pattern of chemotactic factors is not linear [Godiska 1997, Jinquan 1995 and Huber 1991] we tested PMNLs chemotactic activity induced by sequential dilutions of L-CMV and L-1G CCM. L-1G CCM was about 20 fold more chemotactic for PMNLs than L-CMV CCM (FIG. 5b).

Figure 6:
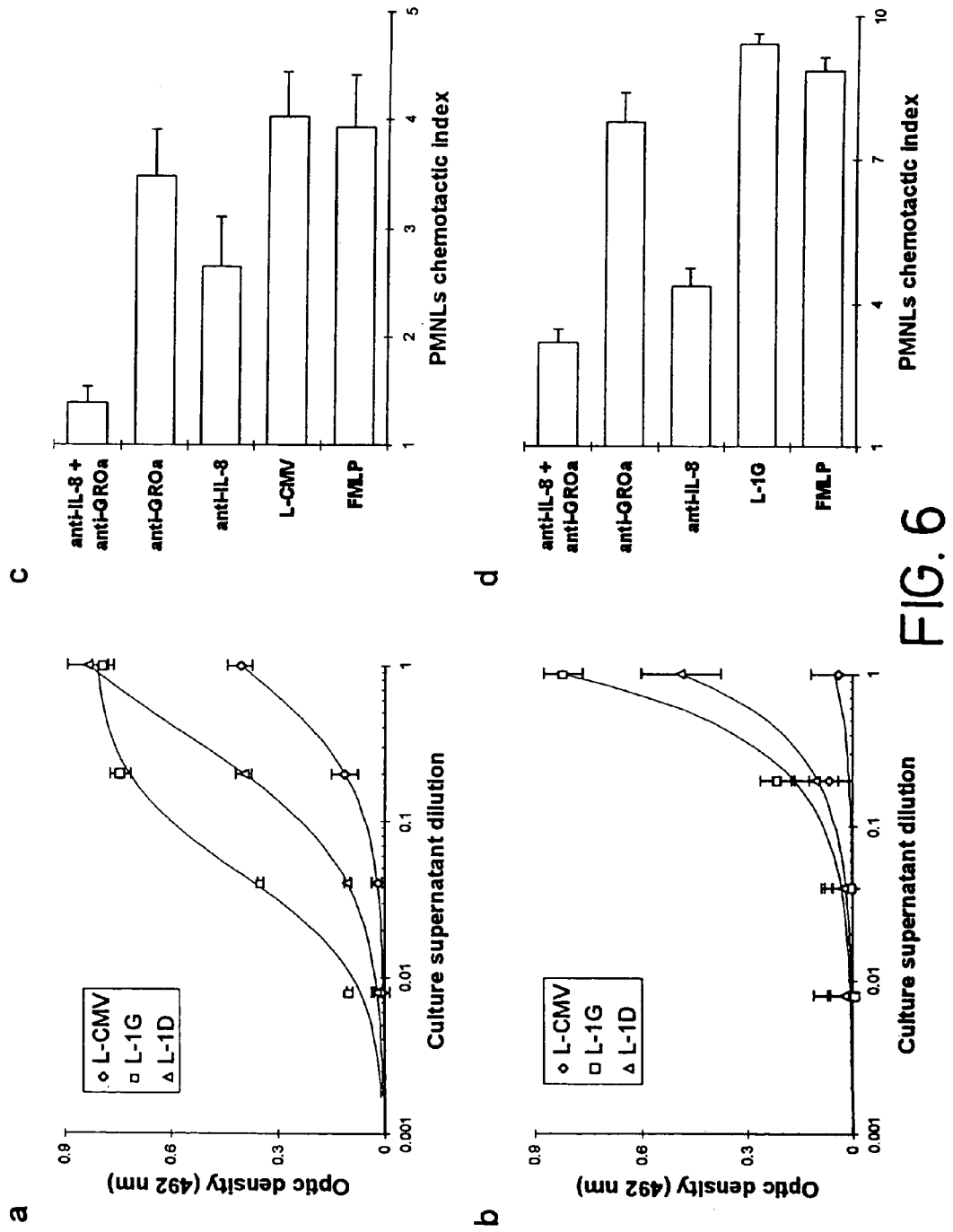
FIG. 6 shows modulation of the production of IL-8 and GROα by SPARC in melanoma cells and shows that both chemokines are involved in PMNLs chemotaxis.

Since melanoma cells might produce CXC chemokines such as IL-8 and GROα which are chemotactic for PMNLs we evaluated the production of these cytokines by the different cell types. ELISA assays showed that L-CMV cells effectively produced both cytokines. Interestingly, IL-8 levels were 20±5 and 5.2±1.9 fold higher in L-1G and L-1D CCM, respectively, than in L-CMV CCM (FIGS. 6a and 6b, p<0.001). Moreover, GROα production by L-CMV cells was below the sensitivity of the assay (<10 pg/ml), while L-1G and L-1D cells produced 400 pg/ml and 250 pg/ml GROα, respectively.

Migration blocking experiments showed that IL-8 and GROα were the unique PMNLs chemotactic factors present in L-CMV CM. While neutralizing anti-IL-8 and anti-GROα monoclonal antibodies showed only partial inhibition of PMNLs chemotaxis induced by L-CMV CCM (30±16%, p<0.05 and 41±23%, p<0.01), the combination of both antibodies completely abolished PMNLs migration suggesting a role for both chemokines in PMNLs chemotaxis (p<0.001, FIG. 6c). In contrast, the combination of both antibodies, even at higher concentrations (20 μg/ml), could not abolished the chemotactic activity of L-1G CM, suggesting the presence of yet unidentified chemotactic factors (FIG. 6d).

PMNLs Adhesion to Melanoma Cells

Figure 7:
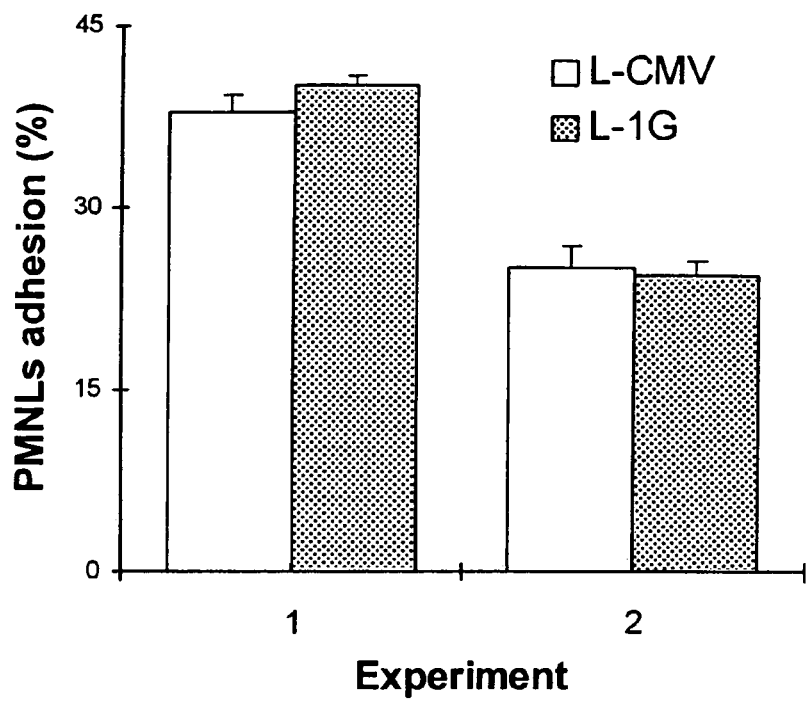
FIG. 7 shows PMNLs adhesion to L-CMV and L-1-G monolayers expressed as the percentage of adherent PMNLs about the total leukocytes used in two independant adhesion assays. No difference was found between the adhesion to L-CMV and SPARC antisense transfected L-1G cells.

Peripheral blood resting PMNLs have a half life of about eight hours. In contrast, tissue activated PMNLs have a prolonged half life, probable due to a blockade in their default apoptotic program. In order to establish whether differences in PMNLs adhesion to SPARC antisense transfectants respect to L-CMV cells could contribute to the increased accumulation of neutrophiis observed in vivo we performed in vitro PMNLs adhesion assays to melanoma monolayers. As shown in FIG. 7, we found no difference in PMNLs adhesion to clone L-1G compared to PMNLs adhesion to L-CMV cells.

Involvement of PMNLs in Tumor Rejection

Figure 8:
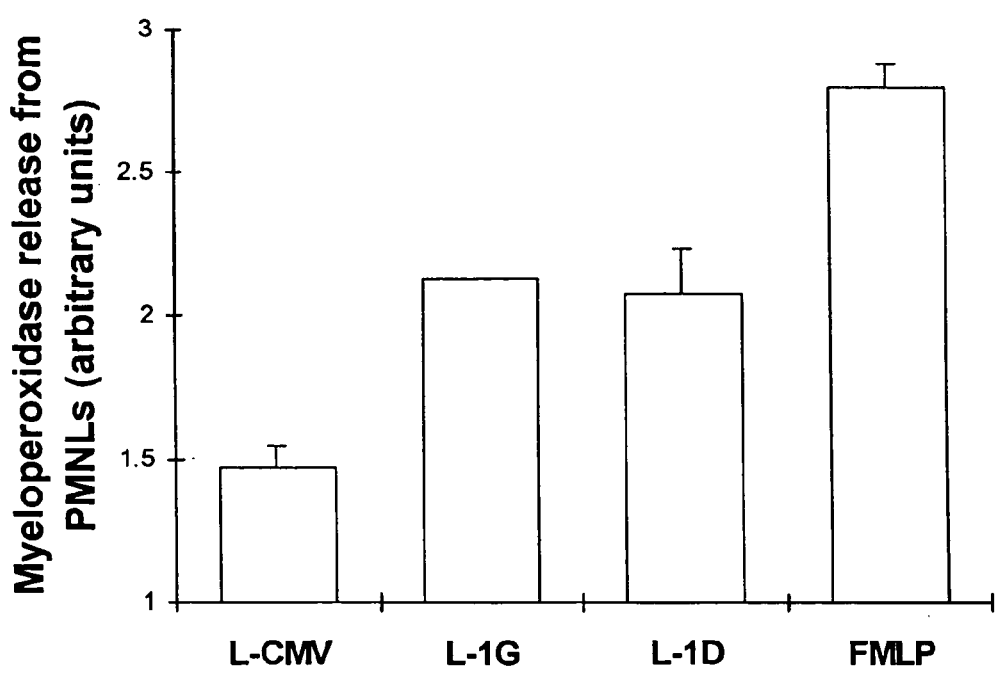
FIG. 8 shows a representative experiement of PMNLs myeloperoxidase release induced by melanoma cell culture supernatant.

The rejection of SPARC antisense transfectants appears to be a non-B non-T cell mediated response, as the rejection was observed in athymic nude mice [Ledda 1997b]. In order to establish whether PMNLs might be activated by human melanoma cells, we studied PMNLs degranulation. L-CMV CM was able to induce PMNLs degranulation, as assessed by myeloperoxidase release (p<0.001, 9 experiments). Moreover, L-1G and L-1D CM were more effective than L-CMV CM as inducers of PMNLs degranulation (p<0.001, 9 experiments) (FIG. 8).

TABLE 1

Cell adhesion to matrigel. Cells were plated on 96-well plates as described in Methods

| Cell Type | Adhesion to matrigel (Cells/field) |
|---|---|
| L-βgal (5 × 10$^4$ cells) | 46.6 ± 5.5a |
| L-1D (5 × 10$^4$ cells) | 1.5 ± 1.1 |
| L-βgal + L-1D (2.5 × 10$^4$ cells of each) | 17.9 ± 3.1 |
| L-βgal + L-1D (5 × 10$^4$ cells of each) | 40.5 ± 5.1 | a: mean ± SD

TABLE 2

βgalactosidase activity of cells which did not adhere to matrigel. Cells were plated on 96-well plates as described in Methods. Cells which did not adhere to matrigel were plated on plastic dishes and stained for βgalactosidase activity.

| Cell Type | L-βgal-positive (cells/field) | L-βgal-negative (cells/field) |
|---|---|---|
| L-βgal (5 × 10$^4$ cells) | No | NO |
| L-1D (5 × 10$^4$ cells) | 0 | 38 ± 2.3a |
| L-βgal + L-1D (2.5 × 10$^4$ cells of each) | 1.8 ± 0.5 | 19.5 ± 2.3 |
| L-βgal + L-1D (5 × 10$^4$ cells of each) | 3.5 ± 0.8 | 37.8 ± 2.1 | a: mean ± SD

TABLE 3

In vivo growth of SPARC antisense transfected cells

| Cell Types | | | | | |
|---|---|---|---|---|---|
| | L-βgal | Parental cells | L-βgal + L-1D (1:1)a | Parental cells + L-1D (1:1) | Parental cells + L-1D (3:2) | Parental cells + L-1D (4:1) |
| Experiment 1 | 5/5b | | 0/5 | | | |
| Experiment 2 | | 6/7 | | 0/8 | 0/8 | 0/8 |
| Experiment 3 | | 7/7 | | | | 0/7 | a: ratio of co-injected cells
b: mice which developed tumors/total number of injected mice Thus, according to the invention, SPARC modulates the production of IL-8 and GROα, both members of the CXC chemokine family, suggesting a role of this glycoprotein in the modulation of immune responses. Downregulation of SPARC induced an overproduction of both IL-8 and GROα by melanoma cells, which correlated with a strong PMNLs in vivo accumulation and in vitro chemotaxis and activation.

Downregulation of SPARC completely prevented tumor formation in nude mice and induced a dominant "bystander" effect leading to the elimination of parental cells expressing SPARC. Since no direct effect of SPARC antisense transfected cells on parental cells was observed, the evidence indicate that in the recited embodiments of the invention PMNLs recruitment and activation was responsible for the bystander killing of parental human melanoma cells.

References by number to certain of the publications indicated above are as follows:—

[1] Stetler-Stevenson W. G., Aznavoorian S., & Liotta L. A., Tumor cell interactions with the extracellular matrix during invasion and metastasis. Annu. Rev. Cell Biol. 9, 541–573 (1993)

[2] Stetler-Stevenson, W. G., Liotta, L. A., & Kleiner, D. E., Extracellular matrix 6: role of matrix metalloproteinases in tumor invasion and metastasis. Faseb J. 7. 1434–1441 (1993)

[3] Albelda S. M., Role of integrins and other cell adhesion molecules in tumor progression and metastasis. Lab. Invest. 68, 4–17 (1993)

[4] Wewer, U. M., Taraboletti, G., Sobel, M. E., Albrechtsen, R., and Liotta, L. A., Role of laminin receptors in tumor cell migration. Cancer Res. 47, 5691–98 (1987)

[5] Lane, T. F., & Sage, E. H., The biology of SPARC, a protein that modulates cell-matrix interactions. FASEB J. 8, 163–173 (1994)

[6] Sage, E. H., & Bornstein, P., Extracellular proteins that modulate. cell-matrix interactions. J. Biol. Chem. 266, 14831–14834 (1991)

[7] Tremble, P. M., Lane, T. F., Sage, E. H., & Werb, Z., SPARC, a secreted protein associated with morphogenesis and tissue remodelling, induces expression of metalloproteinases in fibroblasts through a novel extracellular matrix-dependent pathway. J. Cell Biol. 121, 1433–1444 (1993)

[8] Porter, P. L., Sage, E. H., Lane, T. F., Funk, S. H., & Gow, A. M., Distribution of SPARC in normal and neoplastic tissue. J Histochem Cytochem. 43, 791–800 (1995)

[9] Podhajcer, O. L. et al., Comparative expression of the SPARC and stromelysin-3 genes in mammary tumors. The Breast 5, 13–20 (1996)

[10] Bellahcene, A., & Castronovo, V., Increased expression of osteonectin and osteopontin, two bone matrix proteins, in human breast cancer. Amer J Pathol 146, 95–100 (1995)

[11] Porte, H., et al., Neoplastic progression of human colorectal cancer is associated with overexpression of the stromelysin-3 and BM-40/SPARC genes. Int. J. Cancer 64, 70–75 (1995)

[12] Podhajcer, O. L., et al., Expression of cathepsin D in primary and metastatic human melanoma and dysplastic nevi. J. Invest. Dermatol. 104, 340–144 (1995)

[13] Terranova, V. P., Williams, J. E., Liotta, L. E., & Martin, G. R., Modulation of the metastatic activity of melanoma cells by laminin and fibronectin. Science 226, 982–985 (1984)

[14] Kanemoto, T., et al., Identification of an amino acid sequence from the laminin A chain that stiumlates metastasis and collagenase IV production. Proc. Natl. Acad. Sci. (USA) 87, 2279–2283 (1990)

[15] Seftor, R. E. B., et al., Role of the alphaVbeta integrin in human melanoma cell invasion. Proc. Natl. Acad. Sci. (USA) 89, 1557–1561 (1992)

[16] Seftor, R. E. B., Sefton, E., Stetler-Stevenson, W. G., & Hendrix, M. J. C., The 72 kDa type IV collagenase is modulated via differetial expression of alphaVbeta3 and alpha5beta1 integrins during human malanoma invasion. Cancer Res. 53, 3411–3415 (1993)

[17] Sage, E. H., Vernon, R. G., Funk, S. E., Everitt, E. A, & Angello, J., SPARC, a secreted protein associated with cellular proliferation, inhibits cell spreading in vitro and exhibits Ca2+-dependent binding to the extracellular matrix. J. Cell Biol. 109, 341–356 (1989)

[18] Lane, T. F., Iruela-Arispe, M & Sage, E. H., Regulation of gene expression by SPARC during angiogenesis in vitro. Changes in fibronectin, thrombospondin-1 and plasminogen activator inhibitor-1. J. Biol. Chem. 267, 16736–16745 (1992)

[19] Kamihagi, K., Katayama, M., Ouchi, R., & Kato, I., Osteonectin/SPARC regulates extracellular secretion rates of fibronectin and laminin extracellular matrix proteins. Biochem. Biophys. Res. Commun. 200, 423–428 (1994)

[20] Maurer P., et al., High-affinity and low-affinity calcium binding and stability of the multidomain extracellular 30-kDa basement membrane glycoprotein (MB-40-SPARC/osteonectin). Eur. J. Biochem. 205, 233–240 (1992)

[21] Lane, T. F. & Sage, E. H., Functional mapping of SPARC: peptides from two distinct sites modulate cell adhesion. J. Cell Biol. 111, 3065–3076 (1990)

[22] Pottgiesser, J. et al., Changes in calcium and collagen II binding caused by mutations in the EF hand and other domains of extracellular matrix protein BM-40 (SPARC, osteonectin). J. Mol. Biol. 238, 563–574 (1994)

[23] Funk, S. E. & Sage, E. H., Differential effects of SPARC and cationic SPARC peptides on DNA synthesis by endothelial cells and fibroblasts. J. Cell Physiol. 154, 53–63 (1993)

[24] Lane, T. F., Iruela-Arispe, M. L., Johnson, R. S. & Sage, E. H., SPARC is a source of copper-binding peptides that stimulate angiogenesis. J. Cell Biol. 125, 929–943 (1994)

[25] Kochevar, G. J., Stanek, J. A. & Rucker, E. B., Truncated fibronectin. An autologous growth-promoting substance secreted by renal carcinoma cells. Cancer 69, 2311–2315 (1992)

[26] Lambert Vidmar, S., Lottspeich, F., Emod, Y., Planchenault, T. & Kleil-Dlouha, V., Latent fibronectin-degrading serine proteinase activity in N-terminal heparin-binding domain of human plasma fibronectin. Eur. J. Biochem. 201, 71–77 (1991)

[27] Mok, S. C., Chan, W. Y., Wong, K. K., Muto, M. G., & Berkowitz, R. S., SPARC, an extracellular matrix protein with tumor-suppressing activity in human ovarian epithelial cells. Oncogene 12, 1895–1901 (1996)

[28] Funk, S. E. & Sage E. H. The Ca2+-binding glycoprotein SPARC modulates cell cycle progression in bovine aortic endothelial cells. Proc. Natl. Acad. Sci. USA 88, 2648–2652 (1991)

[29] Everitt, E. A., & Sage, E. H. Expression of SPARC is correlated with altered morphologies in transfected F9 embryonal carcinoma cells. Exp. Cell Res. 199, 134–146 (1992)

[30] Oppenhein, J. J., Zachariae, C. O. C., Mukaida, N. & Matsushima, K., Properties of the novel proinflammatory supergen "intercrine" cytokine family. Annu. Rev. Immunol. 9, 617–648 (1991)

[31] Gilat, D., Cahalon, L., Harshkovitz, R., & Lider, O., Interplay of T Cells and cytokines in the context of enzymatically modified extracellular matrix. Immunol. Today, 17, 16–20 (1996)

[32] Mercola, D., & Cohen, J. S., Antisense approaches to cancer gene therapy. Cancer Gene Ther. 2, 47–59 (1995)

[33] Trojan, J., et al., Treatment and prevention of rat glioblastoma by immunogenic C6 cells expressing antisense insulin-like growth factor I RNA. Science 259, 94–97 (1993)

[34] Laird, A. D., Brown, P. I., & Fausto, N., Inhibition of tumor growth in liver epithelial cells transfected with a transforming growth factor alpha antisense gene. Cancer Res. 54, 4224–4232 (1994).

[35] Aoki, K., Yoshida, T., Sugimura, T., & Terada, M. Liposome-mediated in vivo gene transfer of antisense K-ras construct inhibits pancreatic tumor dissemination in the murine peritoneal cavity. Cancer Res. 55. 3810–3816 (1995)

[36] Harlow E, Lane D., Antibodies: A laboratory Manual. Chapter 5: Immunizations. Cold Spring Harbor Laboratory, 1988, pp. 53–138

[37] Rao, J. S., et al., Elevated levels of Mr 92,000 type IV collagenase in human brain tumors. Cancer Res. 53, 2208–2211 (1993)

[38] Yabkowitz R, Mansfield P J, Dixit V M and Suchard S J, Motility of human carcinoma cells in response to thrombospondin: relationship to metastatic potential and thrombospondin structural domains. Cancer Res 53, 378–387 (1993)

[39] Collier, I. E., et al., H-ras oncogene-transformed human bronchial epithelial cells (TBE-1) secrete a single metalloprotease capable of degrading basement membrane collagen. J. Biol. Chem. 263, 6579–6587 (1988)

The invention is susceptible of numerous modifications and variations which will be apparent to the person skilled in the art in the light of this disclosure. The scope of the present disclosure is intended to include modifications and variations, as well as combinations and subcombinations of the features mentioned herein. All documents cited are hereby incorporated by reference in their entirety.

The invention claimed is:

1. A method of treating a melanoma tumour in a human, comprising subcutaneously injecting to cells of said tumour an antisense nucleic acid molecule comprising a sequence that is the complement of nucleotides 15–1698 of SEQ ID NO:1.

2. The method of claim 1, wherein said antisense nucleic acid molecule is administered via direct injection to the tumour.

3. The method of claim 1, wherein said antisense nucleic acid molecule is a DNA molecule.

4. The method of claim 1, wherein said antisense nucleic acid molecule is a DNA molecule.

* * * * *